(12) United States Patent
Brown et al.

(10) Patent No.: US 11,104,646 B2
(45) Date of Patent: *Aug. 31, 2021

(54) SMALL MOLECULE ANDROGEN RECEPTOR INHIBITORS AND METHODS OF USE THEREOF

(71) Applicant: GEORGETOWN UNIVERSITY, Washington, DC (US)

(72) Inventors: Milton L. Brown, Brookeville, MD (US); Shujie Hou, Gaithersburg, MD (US); Partha Banerjee, Rockville, MD (US); Karishma Amin, San Francisco, CA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/661,510

(22) Filed: Oct. 23, 2019

(65) Prior Publication Data
US 2020/0247751 A1 Aug. 6, 2020

Related U.S. Application Data

(63) Continuation of application No. 16/182,720, filed on Nov. 7, 2018, now Pat. No. 10,487,056, which is a continuation of application No. 15/749,383, filed as application No. PCT/US2016/045133 on Aug. 2, 2016, now Pat. No. 10,173,978.

(60) Provisional application No. 62/201,291, filed on Aug. 5, 2015.

(51) Int. Cl.
*C07D 209/88* (2006.01)
*A61K 45/06* (2006.01)
*A61P 35/00* (2006.01)
*A61K 31/403* (2006.01)

(52) U.S. Cl.
CPC .......... *C07D 209/88* (2013.01); *A61K 31/403* (2013.01); *A61K 45/06* (2013.01); *A61P 35/00* (2018.01)

(58) Field of Classification Search
CPC ...... C07D 209/88; A61K 31/403; A61P 35/00
USPC .......................................... 548/440; 514/411
See application file for complete search history.

(56) References Cited

U.S. PATENT DOCUMENTS

| | | | |
|---|---|---|---|
| 10,173,978 B2 | 1/2019 | Brown et al. | |
| 10,266,490 B2 | 4/2019 | Rosen et al. | |
| 10,487,056 B2* | 11/2019 | Brown | A61K 45/06 |
| 2003/0040538 A1* | 2/2003 | Miyoshi | A61P 3/10 |
| | | | 514/411 |
| 2005/0215577 A1 | 9/2005 | Dehmlow et al. | |
| 2010/0130579 A1* | 5/2010 | Banerjee | A61P 35/00 |
| | | | 514/411 |
| 2011/0152339 A1 | 6/2011 | Brown et al. | |
| 2013/0066932 A1 | 3/2013 | Mandal et al. | |
| 2015/0044293 A1 | 2/2015 | Rosen et al. | |
| 2018/0215712 A1 | 8/2018 | Brown et al. | |

FOREIGN PATENT DOCUMENTS

| | | |
|---|---|---|
| WO | 2010019271 | 2/2010 |
| WO | 2013136600 | 9/2013 |
| WO | 2017023916 | 2/2017 |

OTHER PUBLICATIONS

Cecil Textbook of Medicine, edited by Bennet, J.C., and Plum F., 20th edition,vol. 1, 1004-1010, 1996.*
Dermer et al., Bio/Technology, 1994, 12:320.*
Freshney et al.,Culture of Animal Cells, A Manual of Basic Technique, Alan R. Liss, Inc., 1983, New York, p. 4.*
Golub et al., Science, 286, 531-537, 1999.*
"PubChem Compound No. CID 44623951 (AGN-PC-079P6V)", National Center for Biotechnology Information, PubChem Compound Database; CID=44623951, Available online at: https://pubchem.ncbi.nlm.nih.gov/compound/44623951, Mar. 1, 2010, 12 pages.
"PubChem Compound No. CID 45379599 (AGN-PC-07CK5H)", National Center for Biotechnology Information. PubChem Compound Database; CID=45379599, Available online at : https://pubchem.ncbi.nlm.nih.gov/compound/45379599, May 17, 2010, 12 pages.
U.S. Appl. No. 15/749,383, "Corrected Notice of Allowability", dated Jul. 18, 2018, 3 Pages.
U.S. Appl. No. 15/749,383 , "Notice of Allowance", dated Jun. 26, 2018, 14 pages.
U.S. Appl. No. 15/749,383 , "Notice of Allowance", dated Aug. 16, 2018, 6 pages.
U.S. Appl. No. 16/182,720 , "Non-Final Office Action", dated Dec. 21, 2018, 14 pages.
U.S. Appl. No. 16/182,720 , "Notice of Allowance", dated Jul. 16, 2019, 6 pages.
Amin et al., "A Naturally Derived Small Molecule Disrupts Ligand-Dependent and Ligand-Independent Androgen Receptor Signaling in Human Prostate Cancer Cells", Mol Cancer Ther., vol. 13, Issue 2, Feb. 2014, pp. 341-352.
Appukkuttan et al., "Microwave-Enhanced Cadogan Cyclization: An Easy Access to the 2-Substituted Carbazoles and Other Fused Heterocyclic Systems", Synlett, No. 1, Letter, 2005, pp. 127-133.
Arora et al., "Glucocorticoid Receptor Confers Resistance to Antiandrogens by Bypassing Androgen Receptor Blockade", Cell., vol. 155, Issue 6, Dec. 5, 2013, pp. 1309-1322.
Asche et al., "Antitumor Carbazoles", Anti-cancer Agents Med Chem., vol. 7 , Issue 2, Mar. 2007, pp. 247-267.

(Continued)

Primary Examiner — Tracy Vivlemore
Assistant Examiner — Ebenezer O Sackey
(74) Attorney, Agent, or Firm — Kilpatrick Townsend & Stockton LLP

(57) ABSTRACT

Small molecule carbazole compounds for use as androgen receptor inhibitors are provided herein. Also provided herein are methods for using the carbazole compounds in treating prostate cancer, including castration-resistant prostate cancer and enzalutamide-resistant prostate cancer. The methods include administering to a subject an effective amount of a compound or composition as described herein.

10 Claims, 18 Drawing Sheets

(56) References Cited

OTHER PUBLICATIONS

Bai et al., "Melanoma Antigen Gene Protein MAGE-11 Regulates Androgen Receptor Function by Modulating the Interdomain Interaction", Molecular and Cellular Biology, vol. 25, No. 4, Feb. 2005, pp. 1238-1257.
Balk, "Androgen Receptor as a Target in Androgen-Independent Prostate Cancer", Urology, vol. 60, Issue 3, Supplement 1, Sep. 2002, pp. 132-138.
Beer et al., "Enzalutamide in Metastatic Prostate Cancer Before Chemotherapy", N Engl J Med., vol. 371, No. 5, Jul. 31, 2014, pp. 424-433.
Cannistra et al., "Ovarian Cancer, Peritoneal Carcinoma and Fallopian Tube Carcinoma", In: Devita VT. Hellman S, Rosenberg SA (eds): Cancer: Principles and Practice of Oncology, 9th Edition, Chapter 104, 2011, 63 pages.
Chen et al., "Interleukin 6 Activates Androgen Receptor-Mediated Gene Expression Through a Signal Transducer and Activator of Transcription 3-Dependent Pathway in LNCaP Prostate Cancer Cells", Cancer Res., vol. 60, Issue 8, Apr. 15, 2000, pp. 2132-2135.
Clegg et al., "ARN-509: A Novel Antiandrogen for Prostate Cancer Treatment", Cancer Res, vol. 72, Issue 6, Mar. 15, 2012, pp. 1494-1503.
Dart et al., "Visualising Androgen Receptor Activity in Male and Female Mice", Plos One, vol. 6, No. 8, Aug. 2013, pp. 1-16.
De Bono et al., "Abiraterone and Increased Survival in Metastatic Prostate Cancer", N Engl J Med., vol. 364, No. 21, May 26, 2011, pp. 1995-2005.
Elattar, et al., "Androgen Receptor Expression is a Biological Marker for Androgen Sensitivity in High Grade Serous Epithelial Ovarian Cancer", Gynecologic Oncology, vol. 124, Issue 1, Jan. 2012, pp. 142-147.
Feldman et al., "The Development of Androgen-Independent Prostate Cancer", Nature Reviews Cancer, vol. 1, No. 1, Oct. 1, 2001, pp. 34-45.
Ferraldeschi et al., "Molecular Pathways: Inhibiting Steroid Biosynthesis in Prostate Cancer", Clin Cancer Res., vol. 19, Issue 13, Jul. 1, 2013, pp. 3353-3359.
Freeman et al., "Triphenylphosphine-Mediated Reductive Cyclization of 2-Nitrobiphenyls: A Practical and Convenient Synthesis of Carbazoles", J Org Chem., vol. 70, No. 13, Jun. 24, 2005, pp. 5014-5019.
Guo et al., "A Novel Androgen Receptor Splice Variant is Up-Regulated During Prostate Cancer Progression and Promotes Androgen Depletion-Resistant Growth", Cancer Res., vol. 69, Issue 6, Mar. 15, 2009, pp. 2305-2313.
Hou et al., "Novel Carbazole Inhibits Phospho-STAT3 through Induction of Protein-Tyrosine Phosphatase PTPN6", Journal of Medicinal Chemistry, vol. 57, No. 15, Jun. 30, 2014, pp. 6342-6353.
Hu et al., "Androgen Receptor Expression and Breast Cancer Survival in Postmenopausal Women", Clinical Cancer Research, vol. 17, Issue 7, Apr. 2011, pp. 1667-1874.
Huggins et al., "The Effects of Castration on Advanced Carcinoma of the Prostate Gland", Arch Surg., vol. 43, No. 21, Aug. 1941, pp. 209-223.
Joseph et al., "A Clinically Relevant Androgen Receptor Mutation Confers Resistance to Second-Generation Antiandrogens Enzalutamide and ARN-509", Cancer Discov., vol. 3, Issue 9, Sep. 2013, pp. 1020-1029.
Korpal et al., "An F676L Mutation in Androgen Receptor Confers Genetic and Phenotypic Resistance to MDV3100 (Enzalutamide)", Cancer Discov., vol. 3, Issue 9, Sep. 2013, pp. 1030-1043.
Labrie et al., "Gonadotropin-Releasing Hormone Agonists in the Treatment of Prostate Cancer", Endocr Rev., vol. 26, Issue 3, May 1, 2005, pp. 361-379.
Li et al., "Androgen Receptor Splice Variants Mediate Enzalutamide Resistance in Castration-Resistant Prostate Cancer Cell Lines", Cancer Research, vol. 73, Issue 2, Jan. 15, 2013, pp. 483-489.
Linja et al., "Amplification and Overexpression of Androgen Receptor Gene in Hormone-Refractory Prostate Cancer", Cancer Res., vol. 61, No. 9, May 1, 2001, pp. 3550-3555.
Long et al., "Discovery of Antitumor Indolocarbazoles: Rebeccamycin, NSC 655649, and Fluoroindolocarbazoles", Curr. Med. Chem., Anticancer Agents, vol. 2, No. 2, Mar. 1, 2002, pp. 255-266.
Nazareth et al., "Activation of the Human Androgen Receptor Through a Protein Kinase a Signaling Pathway", J Biol Chem., vol. 271, No. 33, Aug. 16, 1996, pp. 19900-19907.
International Application No. PCT/US2016/045133, "International Preliminary Report on Patentability", dated Feb. 15, 2018, 6 pages.
International Application No. PCT/US2016/045133, "International Search Report and Written Opinion", dated Oct. 20, 2016, 8 pages.
Prudhomme, "Rebeccamycin Analogues as Anti-Cancer Agents", Eur J Med Chem., vol. 38, Issue 2, Feb. 2003, pp. 123-140.
Sanz et al., "Dioxomolybdenum(VI)-Catalyzed Reductive Cyclization of Nitroaromatics. Synthesis of Carbazoles and Indoles", Adv Synth Catal., vol. 349, Mar. 20, 2007, pp. 713-718.
Scher et al., "Increased Survival With Enzalutamide in Prostate Cancer After Chemotherapy", N Engl J Med., vol. 367, No. 13, Sep. 27, 2012, pp. 1187-1197.
Sharifi et al., "Androgen Deprivation Therapy for Prostate Cancer", Journal of the American Medical Association, vol. 294, No. 2, Jul. 13, 2005, pp. 238-244.
Sheikh et al., "Fluorescent Epigenetic Small Molecule Induces Expression of the Tumor Suppressor Ras-Association Domain Family 1A and Inhibits Human Prostate Xenograft", J Med Chem., vol. 53, No. 6, Mar. 25, 2010, pp. 2376-2382.
Shi et al., "A Survey of Optimization Models on Cancer Chemotherapy Treatment Planning", Annals of Operations Research, vol. 221, No. 1, Oct. 2014, pp, 331-356.
Siegel et al., "Cancer Statistics, 2014", CA Cancer J Clin., vol. 64, No. 1, Jan. 7, 2014, pp. 9-29.
Steinkamp et al., "Treatment-Dependent Androgen Receptor Mutations in Prostate Cancer Exploit Multiple Mechanisms to Evade Therapy", Cancer Research, vol. 69, No. 10, May 15, 2009, pp. 4434-4442.
Sun et al., "Castration Resistance in Human Prostate Cancer Is Conferred by a Frequently or Androgen Receptor Splice Variant", J Clin Invest., vol. 120, Issue 6, Aug. 2, 2010, pp. 2715-2730.
Sun, "Transcriptiomic Profiling of Taxol-Resistant Ovarian Cancer Cells Identitfies FKBP5 and The Androgen Receptor as Critical Markers of Chemotherapeutic Response", Oncotarget, vol. 5, No. 23, Available Online at www.impactjournals.com/oncotarget/, Aug. 25, 2014, pp. 11939-11956.
Taplin et al., "Selection for Androgen Receptor Mutations in Prostate Cancers Treated with Androgen Antagonist", Cancer Research, vol. 59, No. 11, Jun. 1, 1999, pp. 2511-2515.
Tilley et al., "Mutations in the Androgen Receptor Gene Are Associated With Progression of Human Prostate Cancer to Androgen Independence", Clin Cancer Res., vol. 2, Issue 2, Feb. 1996, pp. 277-285.
Tran et al., "Development of a Second-Generation Antiandrogen for Treatment of Advanced Prostate Cancer", Science, vol. 324, Issue 5928, May 8, 2009, pp. 787-790.
Wen et al., "HER-2/neu Promotes Androgen-Independent Survival and Growth of Prostate Cancer Cells Through the Akt Pathway", Cancer Res., vol. 60, Issue 24, Dec. 15, 2000, pp. 6641-6845.
Yeh et al., "From HER2/Neu Signal Cascade to Androgen Receptor and its Coactivators: A Novel Pathway by Induction of Androgen Target Genes Through MAP Kinase in Prostate Cancer Cells", PNAS, U S A., vol. 96, No. 10, May 11, 1999, pp. 5458-5463.

\* cited by examiner

SMALL MOLECULE ANDROGEN RECEPTOR INHIBITORS AND METHODS OF USE THEREOF

CROSS-REFERENCE TO PRIORITY APPLICATION

This application is a continuation of U.S. patent application Ser. No. 16/182,720, filed Nov. 7, 2018, currently pending, which is a continuation of U.S. patent application Ser. No. 15/749,383, filed Jan. 31, 2018, now issued as U.S. Pat. No. 10,173,978, which is a national stage entry of PCT/US2016/045133, filed Aug. 2, 2016, which claims priority to U.S. Provisional Application No. 62/201,291, filed Aug. 5, 2015. These applications are incorporated herein by reference in their entireties.

STATEMENT REGARDING FEDERALLY FUNDED RESEARCH

This invention was made with government support under grant number R01 CA131123 awarded by the National Institutes of Health. The government has certain rights in the invention.

BACKGROUND

Prostate cancer is the most commonly occurring non-skin cancer in men and is estimated to account for 27% of all cancers diagnosed in men in the United States in 2014. The androgen receptor (AR) signaling pathway is found to be highly active in both early- and late-stage prostate cancer. Androgen ablation therapy, which is commonly used to treat advanced prostate cancer, is often effective in causing initial tumor regression. However, patients who progress on androgen ablation therapy develop a more aggressive androgen-independent cancer phenotype known as castration-resistant prostate cancer. The AR signaling pathway retains activity in patients with castration-resistant prostate cancer in spite of the low levels of circulating androgens. Mechanisms that contribute to the retention of AR activity under castrate conditions include AR gene amplification, mutations that render the AR responsive to other steroids and growth factors, crosstalk with survival pathways such as AKT and MAPK, intra-tumoral and adrenal steroidogenesis, and the expression of constitutively active AR splice variants.

Second generation anti-androgens that target the ligand-binding domain (LBD) of the AR have been developed for castration-resistant prostate cancer treatment. Enzalutamide (MDV3100) is currently approved for the treatment of patients with metastatic castration-resistant prostate cancer. ARN-509, a structural analogue of enzalutamide, is currently under Phase III clinical development. In vitro and in vivo studies show that both MDV3100 and ARN-509 inhibit ligand-binding to the AR. Additionally, both agents decrease the transcriptional activity, target gene expression, nuclear localization, and DNA binding of the AR. MDV3100 and ARN-509 are effective in preventing the growth of androgen-dependent VCaP cells in vitro and in decreasing tumor growth in castrate mice in vivo. In a Phase III clinical trial in patients that had progressed on chemotherapy, MDV3100 increased overall survival by approximately five months compared to placebo. A clinical study showed that MDV3100 decreased the risk of radiographic progression and death in chemotherapy naïve men.

Although clinical data indicate the benefits of MDV3100 therapy, evidence indicates the emergence of resistance in castration-resistant prostate cancer (CRPC) cell lines and clinical samples that have undergone prolonged treatment with second generation anti-androgens, MDV3100 and ARN-509. MDV3100 is ineffective in preventing the growth of CRPC cell lines like 22Rv1 unless the AR splice variant, AR-V7, is specifically knocked-down. The appearance of a specific missense mutation (F876L) has been demonstrated in the AR LBD in cell lines, xenograft tumors, and clinical samples that have undergone prolonged treatment with MDV3100 and ARN-509. The appearance of this mutation is accompanied by rising prostate-specific antigen (PSA) levels, indicating resistance to anti-androgen therapy. Additionally, patients who are poor responders to MDV3100 treatment show increased expression of the glucocorticoid receptor (GR) in bone marrow biopsies. Elevated GR expression has been implicated as a compensatory mechanism to overcome AR antagonism in vitro and in vivo. Therefore, the benefits of anti-androgen therapy are short-lived.

SUMMARY

Described herein is an alternative approach to combat emerging resistance that often occurs with current treatments designed to manage prostate cancer. Specifically, provided herein are small molecule carbazole compounds for use as androgen receptor inhibitors. Also provided herein are methods for their use in treating prostate cancer, including castration-resistant prostate cancer and enzalutamide-resistant prostate cancer, in a subject. A class of carbazole compounds described herein includes compounds of the following formula:

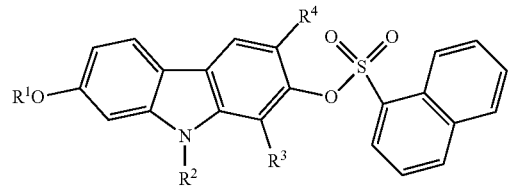

and pharmaceutically acceptable salts thereof. In these compounds, $R^1$ is selected from the group consisting of hydrogen and substituted or unsubstituted $C_1$-$C_6$ alkyl; and $R^2$, $R^3$, and $R^4$ are each independently selected from the group consisting of hydrogen, halogen, amino, substituted or unsubstituted $C_1$-$C_6$ alkyl, and substituted carbonyl. Optionally, $R^1$ is methyl. Optionally, $R^2$ is hydrogen. Optionally, $R^3$ is methyl. Optionally, $R^4$ is hydrogen. Optionally, $R^3$ and $R^4$ are not simultaneously hydrogen. The compound can optionally be

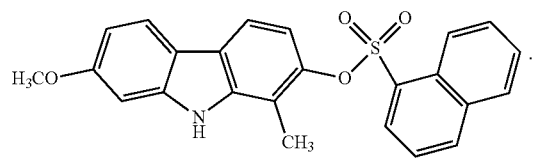 [SMILES: COc1ccc2c(c1)[nH]c1c(C)c(OS(=O)(=O)c3cccc4ccccc34)ccc12]

Also described herein are compositions including a compound as described herein and a pharmaceutically acceptable carrier.

Further described herein are methods of treating or preventing cancer in a subject. The methods of treating or preventing cancer in a subject comprise administering to the subject an effective amount of a composition as described herein. Optionally, the cancer is prostate cancer (e.g., a castration-resistant prostate cancer or a drug-resistant prostate cancer). Optionally, the drug-resistant prostate cancer is an anti-androgen resistant prostate cancer, such as enzalutamide-resistant prostate cancer. The prostate cancer can be an androgen-independent prostate cancer or androgen-dependent prostate cancer.

Optionally, the cancer is breast cancer (e.g., androgen-receptor positive breast cancer). The cancer can optionally be ovarian cancer, such as androgen-receptor positive ovarian cancer. The cancer can optionally be peritoneal cancer (e.g., androgen-receptor positive peritoneal cancer). Optionally, the cancer is fallopian tube cancer (e.g., androgen-receptor positive fallopian tube cancer).

The method can further comprise administering a second therapeutic agent to the subject. The second therapeutic agent can be a chemotherapeutic agent. Optionally, the chemotherapeutic agent is selected from the group consisting of enzalutamide, ARN-509, an Akt inhibitor, a glucocorticoid receptor inhibitor, and a survival factor inhibitor.

Also described herein are methods of inhibiting androgen receptor activity in a cell. The methods comprise contacting the cell with an effective amount of the compound as described herein. The cell can be an androgen-dependent or an androgen-independent cell. The contacting can be performed in vivo or in vitro.

The details of one or more embodiments are set forth in the description and drawings below. Other features, objects, and advantages will be apparent from the description and drawings, and from the claims.

DESCRIPTION OF DRAWINGS

FIG. 8C, lower panel, shows Western blots obtained after treating the cells as described for the upper panel and then harvesting the cells to assess levels of cleaved caspase-3 and cleaved PARP. β-actin was used as a loading control. Data represent mean of three independent experiments with quadruplicate samples; bars, SEM. ***, p value <0.001 determined by ANOVA.

FIG. 13A, lower panel, shows cell viability after treating 22Rv1-MDVR cells with MDV3100 and ARN509 (10 µM) for the indicated period of time.

FIG. 13B, lower panel, shows cell viability after treating VCaP-MDVR cells with MDV3100 and ARN509 (10 µM) for the indicated period of time.

DETAILED DESCRIPTION

Figure 1A:
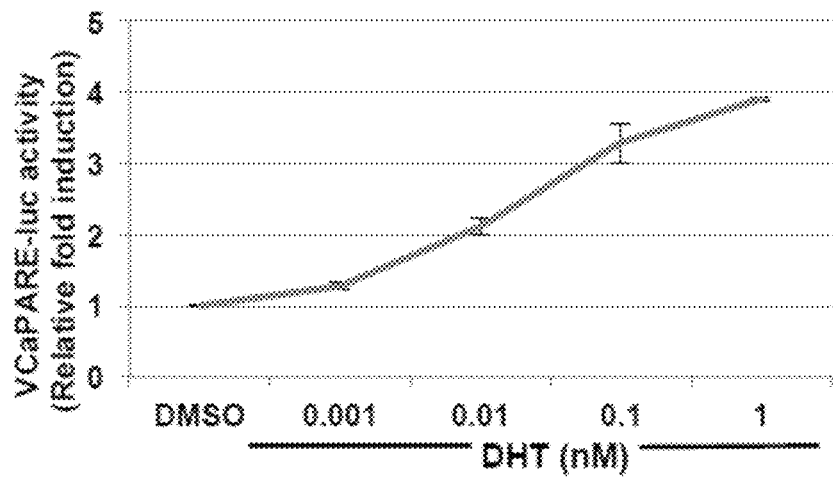
FIG. 1A is a dose-response curve for luciferase activity induction in VCaP-ARE-luc cells upon treatment with DHT for 24 hours. Luciferase activity was measured as a percent of control.

Described herein are small molecule carbazole compounds and methods for their use. The carbozole compounds described herein effectively disrupt androgen receptor (AR) signaling and inhibit growth in castration-resistant and enzalutamide-resistant prostate cancer cells.

I. Compounds

A class of carbazole compounds described herein is represented by Formula I:

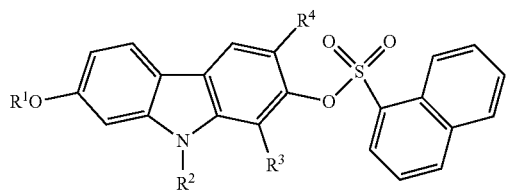

and pharmaceutically acceptable salts thereof.

In Formula I, $R^1$ is selected from the group consisting of hydrogen and substituted or unsubstituted $C_1$-$C_6$ alkyl. Optionally, $R^1$ is $C_1$-$C_4$ alkyl. Optionally, $R^1$ is $C_1$-$C_3$ alkyl. $R^1$ can be, for example, methyl.

Also, in Formula I, $R^2$, $R^3$, and $R^4$ are each independently selected from the group consisting of hydrogen, halogen (e.g., Br, Cl, F, I), substituted or unsubstituted amino, substituted or unsubstituted $C_1$-$C_6$ alkyl, and substituted carbonyl (e.g., acetyl). Optionally, $R^2$ and $R^4$ are each hydrogen. Optionally, $R^3$ is $C_1$-$C_4$ alkyl. Optionally, $R^3$ is $C_1$-$C_3$ alkyl. $R^3$ can be, for example, methyl.

Optionally, in Formula I, $R^3$ and $R^4$ are not simultaneously hydrogen.

An example of Formula I includes the following compound:

SH-I-125

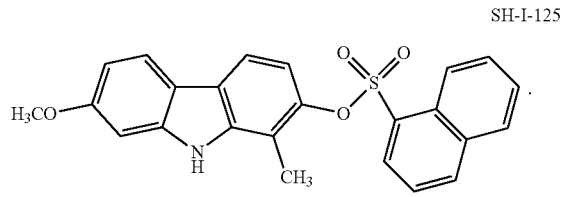 [SMILES: COc1ccc2c(c1)[nH]c1c(C)c(OS(=O)(=O)c3cccc4ccccc34)ccc12]

Additional examples of carbazole compounds useful in the methods described herein include the following compounds:

KED-3-49

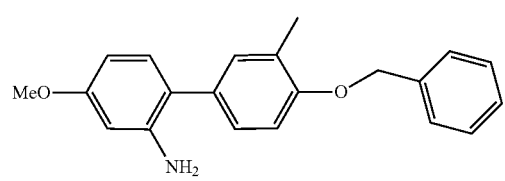

KED-3-79

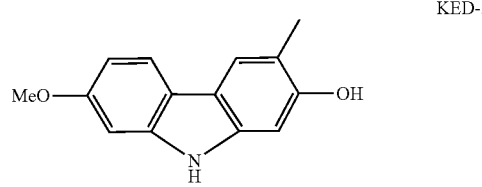

KED-6-51

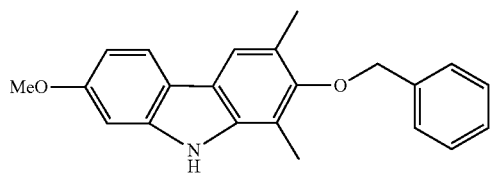

KED-6-57-1

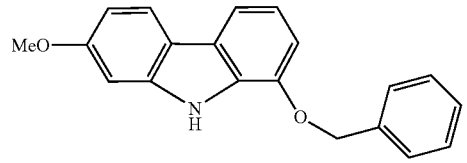

KED-6-57-2

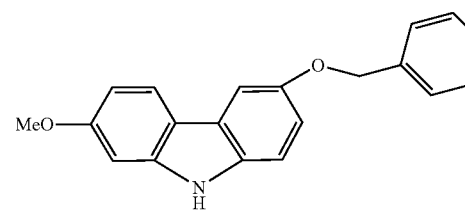

KED-6-59

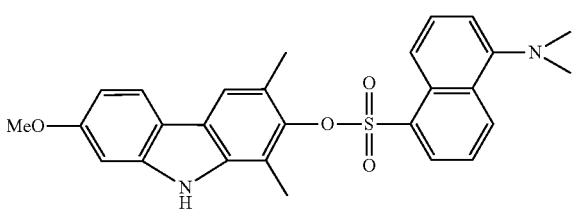

KED-6-75

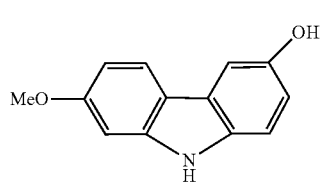

KED-6-77

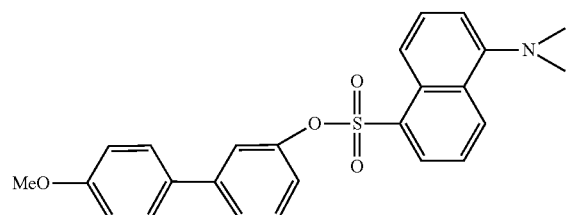

KED-6-79

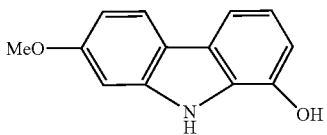

KED-6-85
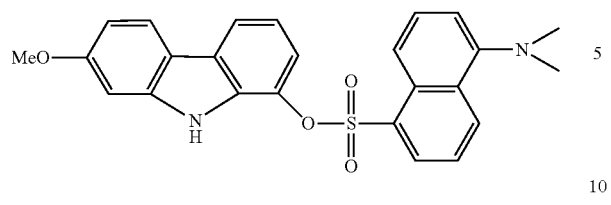
KED-6-161
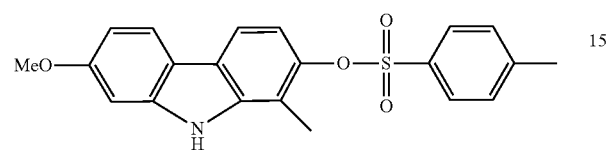
KED-6-163
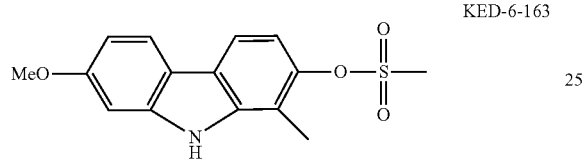
KED-6-167
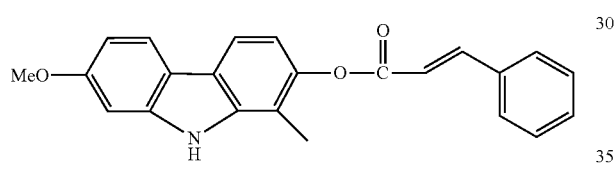
KED-6-169
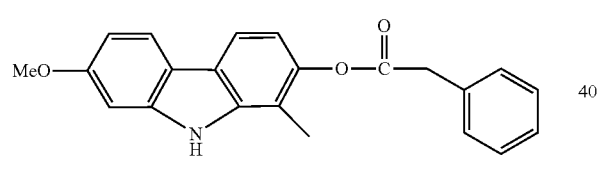
KED-6-171
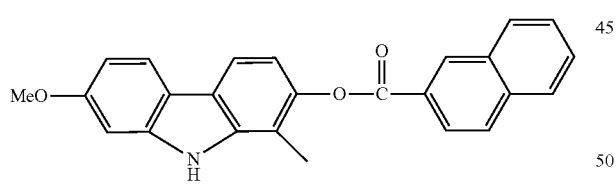
KED-6-173
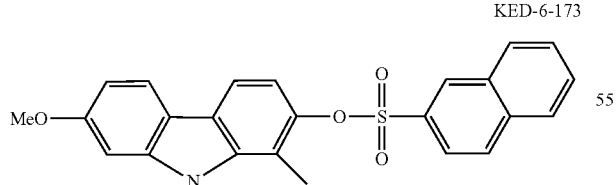
KED-6-181
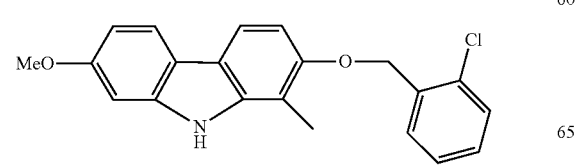
KED-6-189
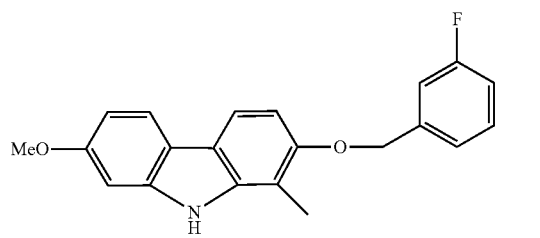
KED-6-185
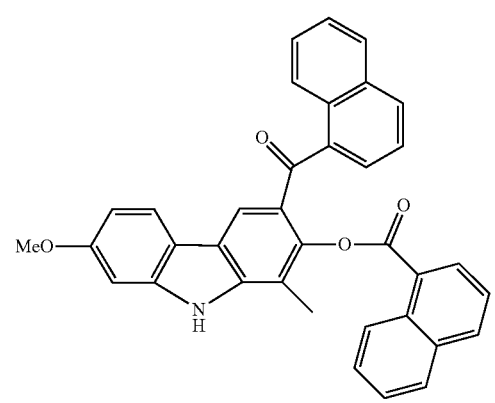
KED-7-15
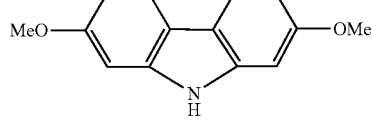
KED-7-19
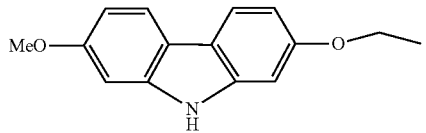
KED-7-21
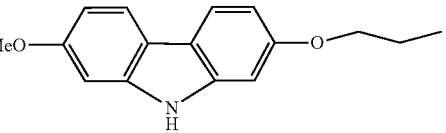
KED-7-51
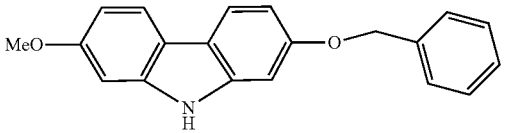
KED-7-55
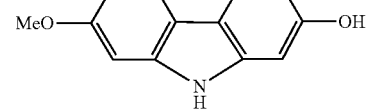

KED-7-59-1
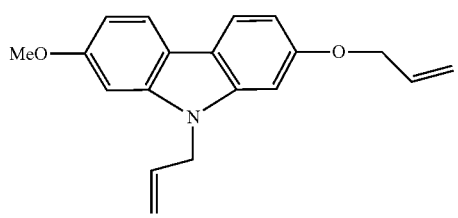
KED-7-59-2
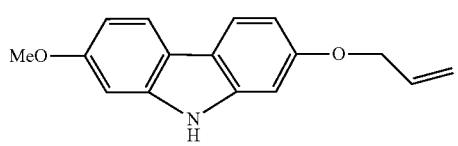
KED-61-1
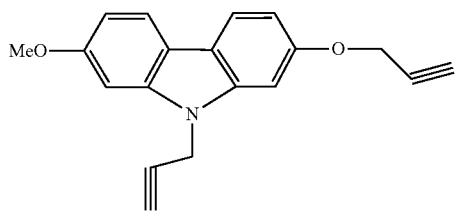
KED-61-2
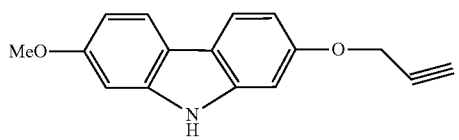
SH-I-2
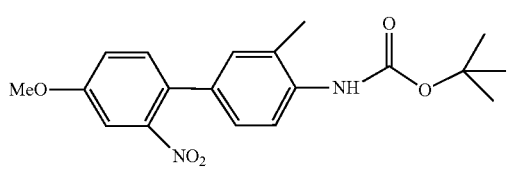
SH-I-5
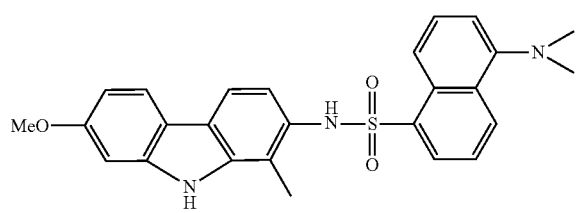
SH-I-6
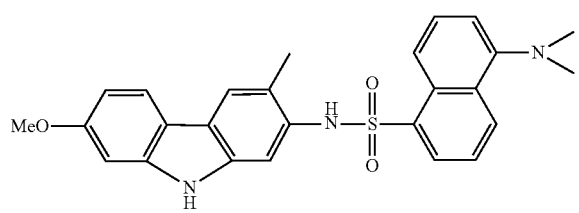
SH-I-12
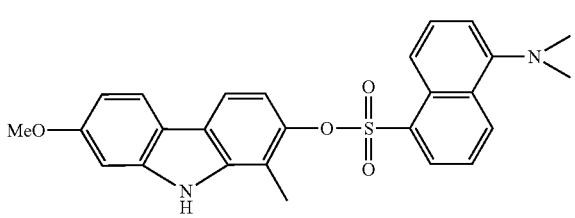
SH-I-14
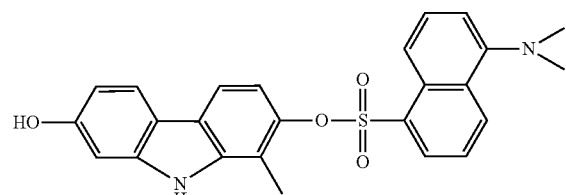
SH-I-17
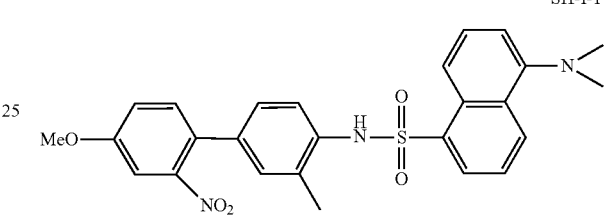
SH-I-18
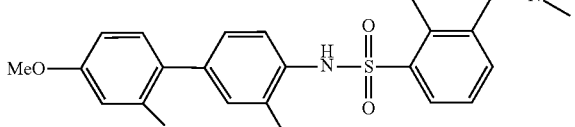
SH-I-19
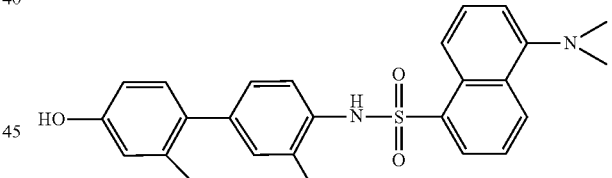
SH-I-20
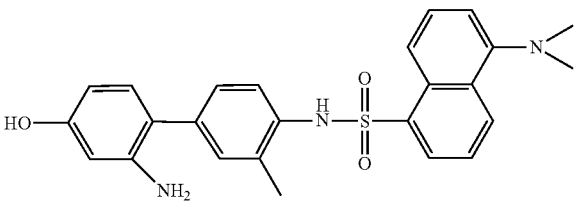
SH-I-21
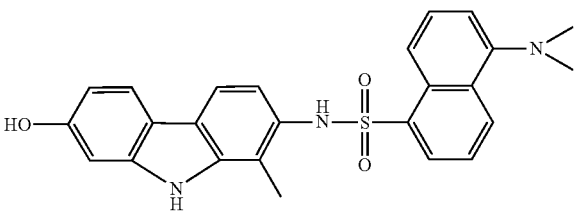

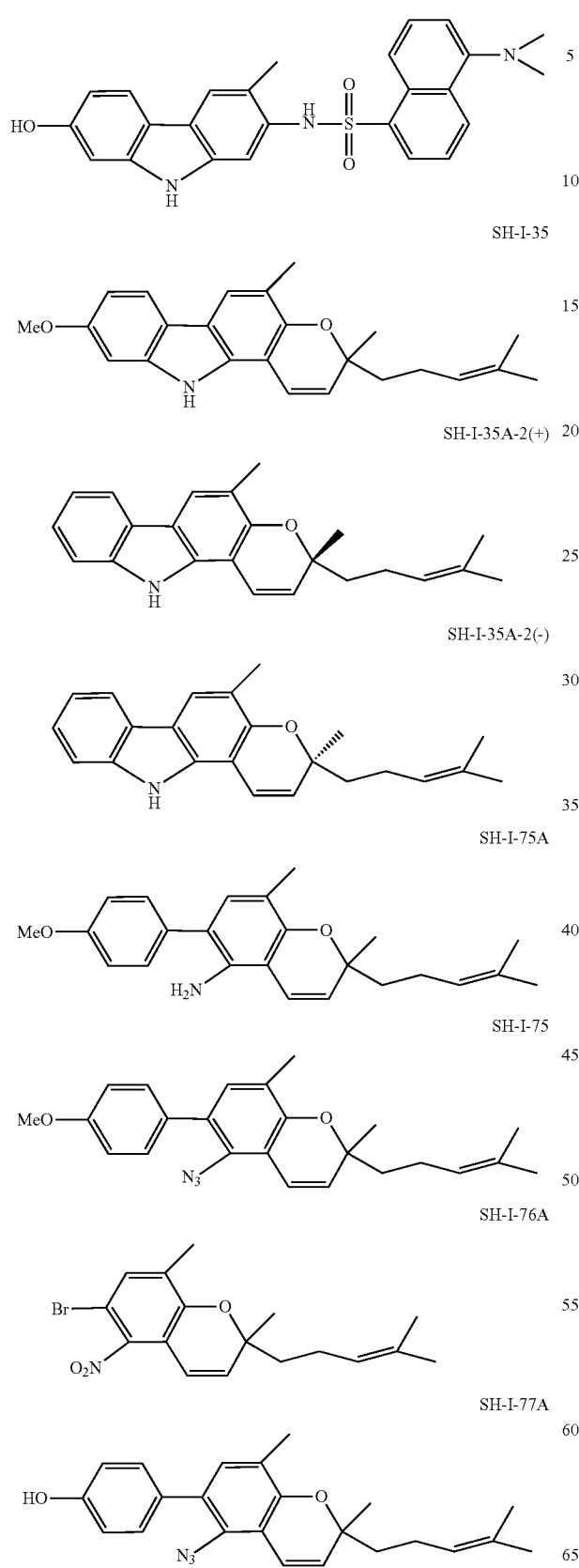
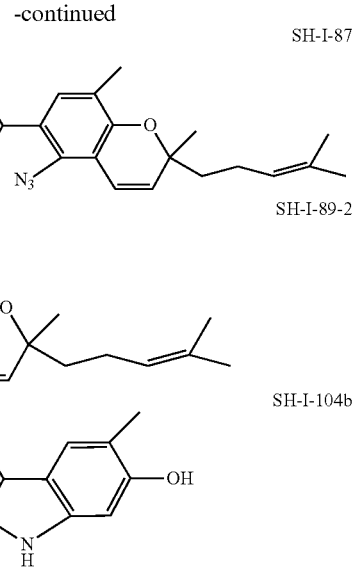

As used herein, the term substituted is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms substitution or substituted with include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term alkyl as used herein is a branched or unbranched saturated hydrocarbon group of 1 to 6 carbon atoms, such as methyl, ethyl, n-propyl, iso-propyl, n-butyl, sec-butyl, iso-butyl, tert-butyl, n-pentyl, isopentyl, neopentyl, n-hexyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

The terms amine or amino as used herein are represented by the formula $-NZ^1Z^2$, where $Z^1$ and $Z^2$ can each be a substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group.

The term carbonyl group as used herein is represented by the formula $-C(O)-Z$, where Z is a substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group. Carbonyl group includes carboxylate or carboxyl groups (i.e., groups represented by the formula —C(O)O⁻).

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I and the compounds described herein include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

Compounds described by Formula I and pharmaceutically acceptable salts thereof can be made using the method shown in Scheme 1, which depicts the synthesis of compounds of Formula I wherein $R^2$ is hydrogen.

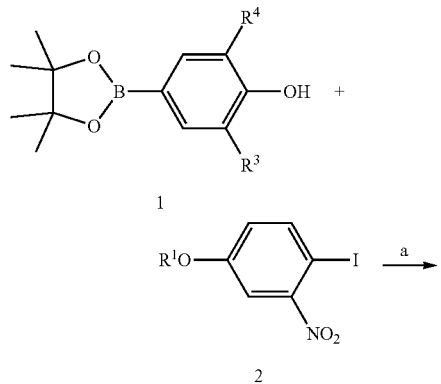

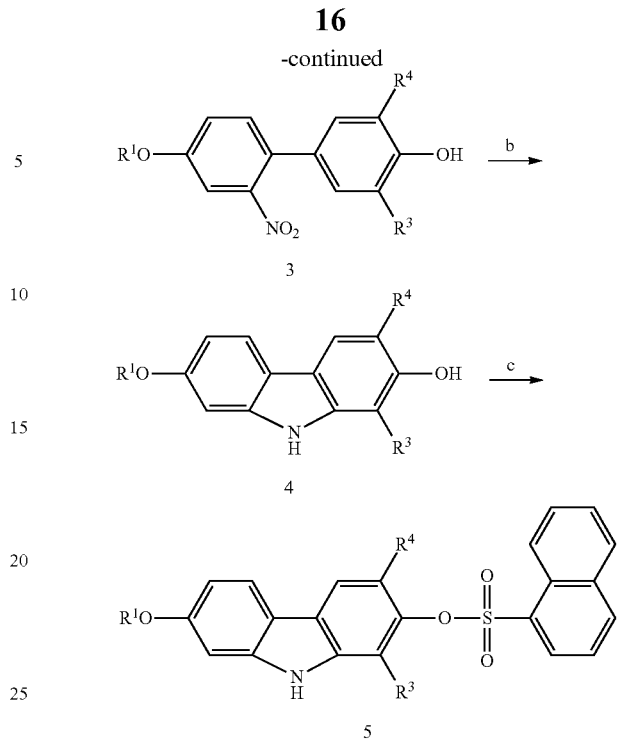

Reagents and conditions: (a) Pd(PPh₃)₄, K₂CO₃, toluene-ethanol-water, reflux; (b) PPh₃, 1,3-DCB, 250° C., 200 W, microwaves; (c) 1-naphthalenesulfonyl chloride, DCM-TEA.

As depicted in Scheme 1, the compounds according to Formula I wherein $R^2$ is hydrogen can be synthesized in three steps. A palladium-catalyzed cross-coupling reaction can be carried out between the 4-hydroxyphenylboronic acid (1) and the iodo-nitrobenzene (2), providing the biphenyl-4-ol compound (3). A one-step cyclization of the 2-nitrobiphenyl system can be performed under microwave conditions to yield carbazole (4). Carbazole (4) can be treated with 1-naphthalenesulfonyl chloride in the presence of trimethylamine to provide the target sulfonic ester (5).

III. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66: 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat, prevent, or ameliorate cancer in a subject. The methods include administering to a subject an effective amount of one or more of the compounds or compositions described herein, or a pharmaceutically acceptable salt or prodrug thereof. Effective amount, when used to describe an amount of compound in a method, refers to the amount of a compound that achieves the desired pharmacological effect or other biological effect. The compounds and compositions described herein or pharmaceutically acceptable salts thereof are useful for treating cancer in humans, including, without limitation, pediatric and geriatric populations, and in animals, e.g., veterinary applications.

Optionally, the cancer is prostate cancer, bladder cancer, brain cancer, breast cancer, colon cancer, cervical cancer, fallopian tube cancer, gastrointestinal cancer, genitourinary cancer, head and neck cancer, lung cancer, ovarian cancer, pancreatic cancer, peritoneal caner, renal cancer, skin cancer, or testicular cancer. The prostate cancer can be androgen-dependent prostate cancer or androgen-independent prostate cancer. As used herein, androgen-dependent prostate cancer means that the cancer cells require high levels of androgens to grow. Androgen-independent prostate cancer means that the cancer cells are not dependent on androgen and can continue to grow even when androgen levels are low or undetectable. In androgen-independent prostate cancer, cancer cell growth can be triggered by ligands other than androgen.

Optionally, the prostate cancer can be castration-resistant prostate cancer. As used herein, castration-resistant prostate cancer refers to prostate cancer that is no longer responsive to castration treatment. Optionally, the prostate cancer is a drug-resistant prostate cancer, such as an anti-androgen resistant prostate cancer (e.g., enzalutamide-resistant prostate cancer or ARN-509 resistant prostate cancer).

Optionally, the cancer can be an androgen-receptor positive cancer. The cancer can be, for example, androgen-receptor positive breast cancer, androgen-receptor positive ovarian cancer, androgen-receptor positive peritoneal cancer, or androgen-receptor positive fallopian tube cancer.

The methods of treating or preventing cancer in a subject can further comprise administering to the subject a therapeutic agent, radiation therapy, or a combination thereof. Thus, the provided compositions and methods can include one or more additional agents. The one or more additional agents and the compounds described herein or pharmaceutically acceptable salts or prodrugs thereof can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiandrogens (e.g., enzalutamide, flutamide, nilutamide, bicalutamide, and ARN-509); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); steroids (e.g., bethamethasone sodium phosphate); Akt inhibitors; glucocorticoid receptor inhibitors (e.g., beclometasone, betamethasone, budesonide, ciclesonide, flunisolide, fluticasone, mifepristone, mometasone, and triamcinolone); and survival factor inhibitors (e.g., inhibitors of neurotrophins, cytokines, epidermal growth factor (EGF), platelet-derived growth factor (PDGF), fibroblast growth factor (FGF), insulin-like growth factor (IGF), heparin-binding epidermal growth factor (HB-EGF), vascular endothelial growth factor (VEGF), pigment epithelium-derived factor (PEDF), schwannoma-derived growth factor (SDGF), hepatocyte growth factor (HGF), transforming growth factor-α (TGF-α), transforming growth factor-β (TGF-β), bone morphogenetic proteins (e.g., BMP1-BMP15), growth differentiation factor-9 (GDF-9), granulocyte-colony stimulating factor (G-CSF), granulocyte-macrophage colony stimulating factor (GM-CSF), myostatin (GDF-8), erythropoietin (EPO), and thrombopoietin (TPO)).

Optionally, the one or more additional agents can include cancer vaccines, such as PROVENGE® (sipuleucel-T; Dendreon Corp., Seattle, Wash.).

Any of the aforementioned additional agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after the development of cancer. Prophylactic administration can occur for several days to years prior to the manifestation of symptoms of cancer. Therapeutic treatment involves administering to a subject a therapeutically effective amount of the compounds and compositions or pharmaceutically acceptable salts thereof as described herein after cancer is diagnosed.

The methods herein for prophylactic and therapeutic treatment optionally comprise selecting a subject with or at risk of developing cancer as described herein. A skilled artisan can make such a determination using, for example, a variety of prognostic and diagnostic methods, including, for example, a personal or family history of the disease or condition, clinical tests (e.g., imaging, biopsy, genetic tests), and the like.

The compounds described herein are also useful in inhibiting androgen receptor activity in a cell. The methods of inhibiting androgen receptor activity in a cell include contacting the cell with an effective amount of one or more of the compounds as described herein. The cell can be an androgen-dependent cell or an androgen-independent cell. Optionally, the contacting is performed in vivo. Optionally, the contacting is performed in vitro.

V. Kits

Also provided herein are kits for treating or preventing cancer in a subject. A kit can include any of the compounds or compositions described herein. For example, a kit can include one or more compounds of Formula I or a salt thereof. A kit can further include one or more additional agents, such as a chemotherapeutic agent. A kit can include an oral formulation of any of the compounds or compositions described herein. A kit can additionally include directions for use of the kit (e.g., instructions for treating a subject), a container, a means for administering the compounds or compositions, and/or a carrier. Kits can include multiple doses (e.g., in a blister pack), can include means for administration (e.g., a delivery device like a syringe), or the like.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: Synthesis

All reagents and solvents were purchased from commercial suppliers and used as received unless noted otherwise. Flash column chromatography separations were done on a Biotage SP1 system (Biotage; Uppsala, Sweden) monitoring at 254 and 310 nm. NMR spectra were recorded on a Varian 400 spectrometer (Agilent Technologies; Santa Clara, Calif.) at 25° C., operating at 400 MHz for $^1$H and 100 MHz for $^{13}$C NMR. The chemical shifts are expressed in ppm downfield from TMS as an internal standard. Reactions were monitored by thin-layer chromatography (TLC) on silica gel 60 glass slides. The structure of the synthesized compounds follows unequivocally from the mode of synthesis and the m/z values found in their low- and high-resolution mass spectra, TLC and NMR spectroscopy verified the purity.

Compound SH-I-125 was synthesized according to the method depicted in Scheme 2. Procedures for each step of the synthesis are provided below.

Scheme 2

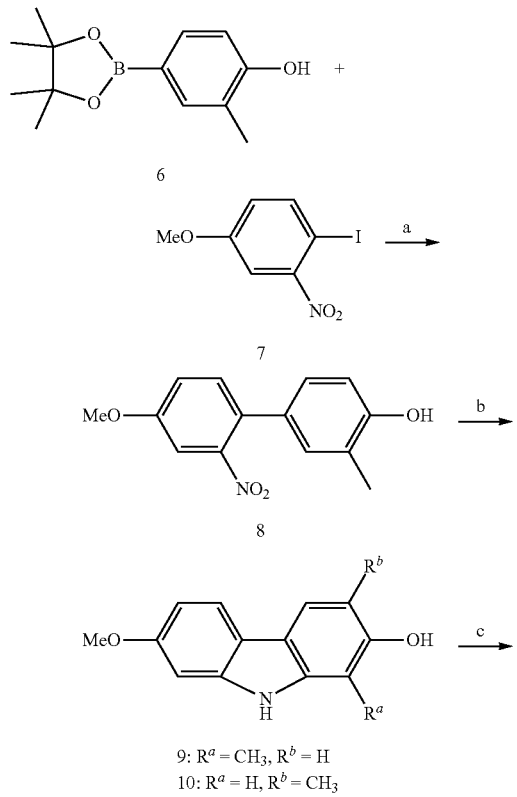

9: $R^a$ = CH$_3$, $R^b$ = H
10: $R^a$ = H, $R^b$ = CH$_3$

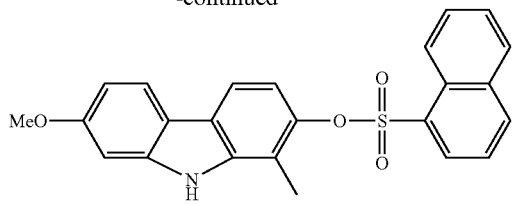

11

Reagents and conditions: (a) Pd(PPh$_3$)$_4$, K$_2$CO$_3$, toluene-ethanol-water, reflux; 87%; (b) PPh$_3$, 1,3-DCB, 250° C., 200 W, microwaves; 42% for 9 and 47% for 10; (c) 1-naphthalenesulfonyl chloride, DCM-TEA, 85%.

4'-methoxy-3-methyl-2'-nitrobiphenyl-4-ol (8)

4-Hydroxyphenylboronic acid (6) (2.3 g, 10 mmol) was added to a solution of 4-iodo-3-nitroanisole (7) (3.1 g, 11 mmol) in toluene-ethanol-water (30 mL, v/v/v=4/2/1), followed by Pd(PPh$_3$)$_4$ (350 mg, 0.3 mmol) and K$_2$CO$_3$ (5.3 g, 50 mmol). The mixture was refluxed for 6 hours. After cooling to room temperature, the mixture was filtered through a celite pad. The filtrate was concentrated, diluted with DCM (100 mL), and washed with saturated brine (3×30 mL). After concentration and chromatography (hexane/acetone=6/1), the product afforded was 4'-methoxy-3-methyl-2'-nitrobiphenyl-4-ol (8) (2.3 g, 87%). $^1$H NMR (400 MHz, CDCl$_3$), δ 7.31 (m, 2H), 7.12 (dd, J=2.8 Hz, 8.4 Hz, 1H), 7.04 (s, 1H), 6.98 (d, J=8.0 Hz, 1H), 6.78 (d, J=8.0 Hz, 1H), 3.88 (s, 3H), 2.26 (s, 3H); $^{13}$C NMR (100 MHz, CDCl$_3$), δ 158.7, 153.7, 132.7, 130.6, 129.5, 128.3, 126.7, 124.1, 118.5, 115.1, 108.8, 55.8, 15.7; MS (TOF-ES$^+$): 260.3 m/z [M+1]$^+$.

7-methoxy-1-methyl-9H-carbazol-2-ol (9) and
7-methoxy-3-methyl-9H-carbazol-2-ol (10)

A mixture of 8 (260 mg, 1 mmol), triphenylphosphine (1.04 g, 4.0 mmol), and 1,3-dichlorobenzene (3 mL) was heated in a microwave (200° C., powermax) for 6 hours. After concentration under reduced pressure and chromatography (toluene/acetone=3/1), compounds 9 (94 mg, 42%) and 10 (107 mg, 47%) were afforded.

7-methoxy-1-methyl-9H-carbazol-2-ylnaphthalene-1-sulfonate (SH-I-125)

1-naphthalenesulfonyl chloride (136 mg, 0.6 mmol) was added to a solution of 9 (90 mg, 0.4 mmol) in anhydrous dichloromethane (2 mL) in the presence of Et$_3$N (0.5 ml) under N$_2$ with stirring at 0° C. After stirring for 2 hours, the mixture was concentrated and chromatographed (hexane/acetone=2/1) to give compound 11 (141 mg, 85%) as a solid. $^1$H NMR (400 MHz, CDCl$_3$), δ 8.82 (d, J=8.4 Hz, 1H), 8.06 (d, J=8.4 Hz, 1H), 8.04 (d, J=7.6 Hz, 1H), 7.91 (d, J=8.4 Hz, 1H), 7.67 (m, 2H), 7.58 (t, J=8.0 Hz, 1H), 7.39 (t, J=8.0 Hz, 1H), 7.35 (d, J=8.4 Hz, 1H), 6.80 (d, J=2.0 Hz, 1H), 6.70 (dd, J=2.0 Hz, J=8.4 Hz, 1H), 6.25 (d, J=8.4 Hz, 1H), 3.76 (s, 3H), 2.28 (s, 3H); $^{13}$C NMR (100 MHz, CDCl$_3$), δ 159.06, 145.29, 141.38, 139.35, 135.53, 134.16, 131.90, 130.92, 128.93, 128.91, 128.67, 127.31, 125.30, 124.00, 121.63, 121.03, 116.98, 116.80, 113.83, 113.48, 1087.72, 94.84, 55.56, 11.23; HRMS (TOF-ES$^+$): m/z [M+1]$^+$ calcd for C$_{24}$H$_{19}$NO$_4$S: 418.1032; found 418.1029.

Example 2: SH-I-125 Activity

The novel carbazole compound SH-I-125 effectively disrupts AR signaling and induces apoptosis in castration-resistant and enzalutamide-resistant (also referred to herein as MDV3100-resistant) prostate cancer cells. The data described below show that SH-I-125 is more effective than both enzalutamide and ARN509. These findings demonstrate the therapeutic capabilities of SH-I-125 for treating castration-resistant prostate cancer and anti-androgen-resistant prostate cancer.

Materials and Methods

Reagents

MDV3100 (Enzalutamide) and ARN-509 were purchased from Selleckchem (Houston, Tex.) and were used in the specified concentrations. DHT (Steraloids; Newport, R.I.) and forskolin (Sigma; St. Louis, Mo.) were used in the concentrations indicated below. MG132 was obtained from Tocris Biosciences (Bristol, UK).

Cell Lines

Prostate cancer cell lines (VCaP and CWR22Rv1) were obtained from American Type Culture Collection (Manassas, Va.) and were cultured in phenol-red free Improved Minimum Essential Media (IMEM) (Invitrogen; Carlsbad, Calif.) containing 10% fetal bovine serum (Atlanta Biologicals; Lawrenceville, Ga.), 2 mM glutamine, 100 U/ml penicillin G sodium, and 100 mg/mL streptomycin sulfate (Sigma; St Louis, Mo.), unless otherwise specified. PrEC, which are non-tumorigenic normal primary prostate epithelial cells, were purchased from Lonza (Walkersville, Md.). VCaP cells were cultured in the above media in the presence of DHT (1 nM) unless otherwise specified. All cell lines used were tested and authenticated by DNA fingerprinting short-tandem repeat (STR) analysis.

Establishment of Stable VCaP- and 22Rv1-ARE-Luciferase Cell Lines

VCaP and CWR22Rv1 (referred to as 22Rv1) cells were transduced with ARE-luciferase Cignal Lenti Pathway Reporter (Qiagen; Valencia, Calif.) and cultured as described above in the presence of 1 μg/mL puromycin. Following antibiotic selection, cells stably expressing ARE-luciferase were isolated, cloned and cultured to generate a stable ARE-reporter cell lines.

Establishment of MDV3100-Resistant VCaP and 22Rv1 Cell Lines

VCaP cells were cultured as described above in the presence of DHT (1 nM) and

MDV3100 (10 μM) for more than 20 passages. Although marginal cell death was noted during early passages, the majority of the cells survived with no cell death occurring in subsequent passages. 22Rv1 cells were cultured as described above, in the presence MDV3100 (10 μM) for more than 20 passages. No cell death was observed, even in early passages.

Western Blotting

Western blotting was performed as described in Amin et al., *Mol. Cancer Ther.*, 13:341-52 (2014). The following antibodies were used: Androgen receptor (N-20; Santa Cruz Biotechnology; Dallas, Tex.), PSA (A0562; Dako; Carpinteria, Calif.), β-actin (SC-47778; Santa Cruz Biotechnology), AR-V7 (AG10008; Precision Antibody; Columbia, Md.), cleaved PARP (9541; Cell Signaling Technologies, Danvers, Mass.), and cleaved caspase-3 (9664; Cell Signaling Technologies, Danvers, Mass.).

Immunofluorescence Staining

Immunofluorescence staining was performed as described in Amin et al., *Mol. Cancer Ther.*, 13:341-52 (2014).

MTT Assay

Cells were treated in the manner indicated below for the specified period of time. MTT assay was performed as described in Amin et al., *Mol. Cancer Ther.*, 13:341-52 (2014).

Live and Dead Cell Staining

Live and dead cells were determined using a Cell Viability/Cytotoxicity Assay kit (Biotium Inc.; Hayward, Calif.).

Quantitative RT-PCR

Quantitative RT-PCR was performed using the protocol and the primers as described in Amin et al., *Mol. Cancer Ther.*, 13:341-52 (2014).

Caspase Activity Assay

22Rv1 cells were plated in equal numbers in a 96-well plate and treated with SH-I-125, MDV3100 and ARN-509 as described below for the indicated periods of time (24-72 hrs), and was followed by caspase 3/7 activity measurement using Caspase-Glo 3/7 Assay (Promega; Madison, Wis.).

Statistical Analyses

All data were derived from at least three independent experiments and statistical analyses were conducted by using one-way analysis of variance (ANOVA) or Student's t test, where applicable. Values were presented as means±SEM. p-value <0.05 was considered significant.

Results

SH-I-125 is an Effective Disruptor of Ligand-Induced AR Signaling Using a Cell-Based Reporter Assay.

Figure 1B:
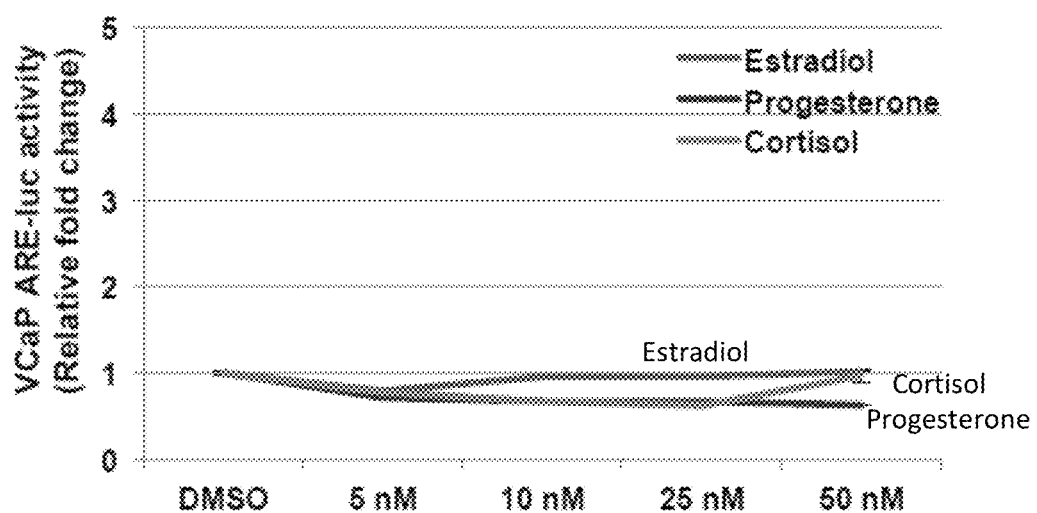
FIG. 1B shows dose response curves for luciferase activity induction in VCaP-ARE-luc cells treated with the indicated concentrations of estradiol, progesterone and cortisol for 24 hours. Luciferase activity was measured as a percent of control.

A cell-based assay was developed to identify potent disruptors of ligand-induced AR signaling with comparable or superior activity to clinical anti-androgens, MDV3100 and ARN-509. Androgen-dependent VCaP cells were made to stably express an androgen-response element luciferase reporter (VCaP-ARE-luc). While this system was highly sensitive to DHT stimulation (FIG. 1A), it was unresponsive to other steroids (FIG. 1B), suggesting that it is specific for measuring AR activation by its ligand.

Figure 2:
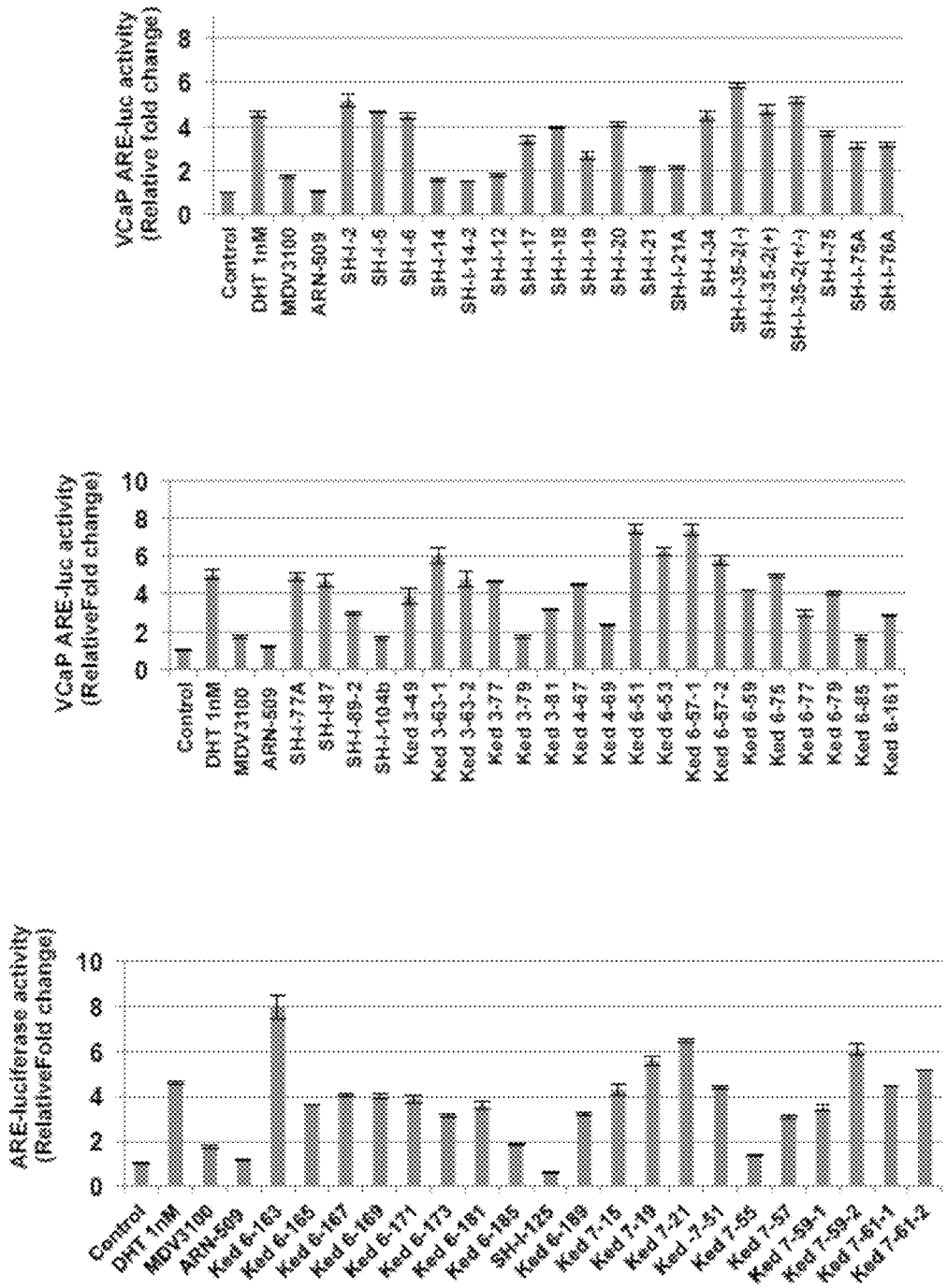
FIG. 2 shows the results of luciferase activity testing on synthetic carbazoles using VCaP-ARE-luc cells. The VCaP-ARE-luc cells were treated with MDV3100 (5 µM), ARN-509 (5 µM), and synthetic carbazoles (5 µM) in the presence of DHT (1 nM) for 24 hours. Luciferase activity was determined relative to the control. Columns, mean of three independent experiments with quadruplicate samples; bars, SEM.

Upon screening the synthetic carbazoles using VCaP-ARE-luc cells, several candidates were identified that disrupted DHT-induced AR transcriptional activity in a manner comparable to MDV3100 and ARN-509 (FIG. 2). Upon further testing, SH-I-125 was identified among these as the most suitable agent.

SH-I-125 is More Potent than Natural Carbazole, Mahanine in Preventing Cell Proliferation and Disrupting AR Signaling.

Figure 3A:
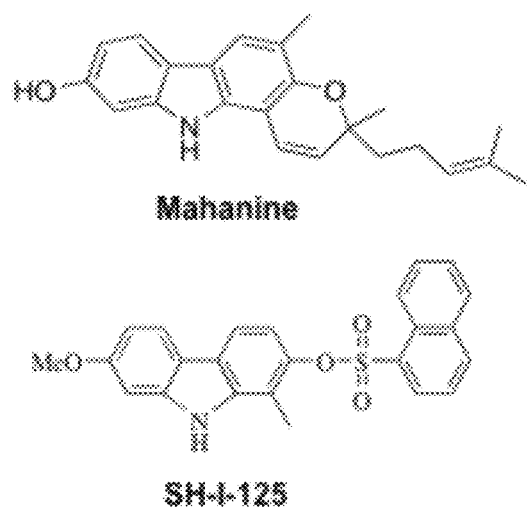
FIG. 3A shows the chemical structure of mahanine (upper panel) and SH-I-125 (lower panel).
Figure 3B:
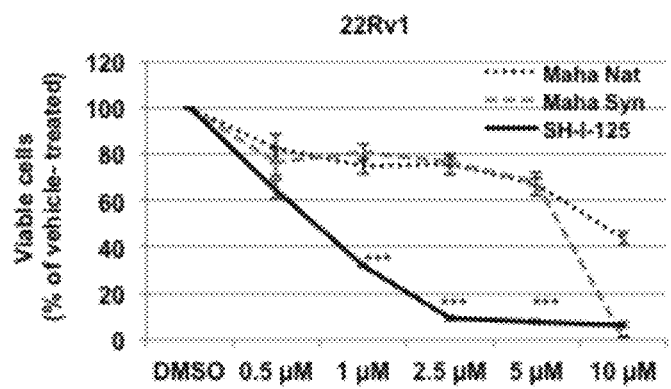
FIG. 3B shows cell viability as determined by MTT assay. 22Rv1 cells were treated with the indicated doses of mahanine (Maha Nat), synthetic mahanine (Maha syn), and SH-I-125 for 3 days. MTT assay was conducted to determine cell viability. The viability of control cells was set at 100%. Data represent mean of three independent experiments with quadruplicate samples; bars, SEM. ***, p value <0.001 determined by ANOVA.
Figure 3C:
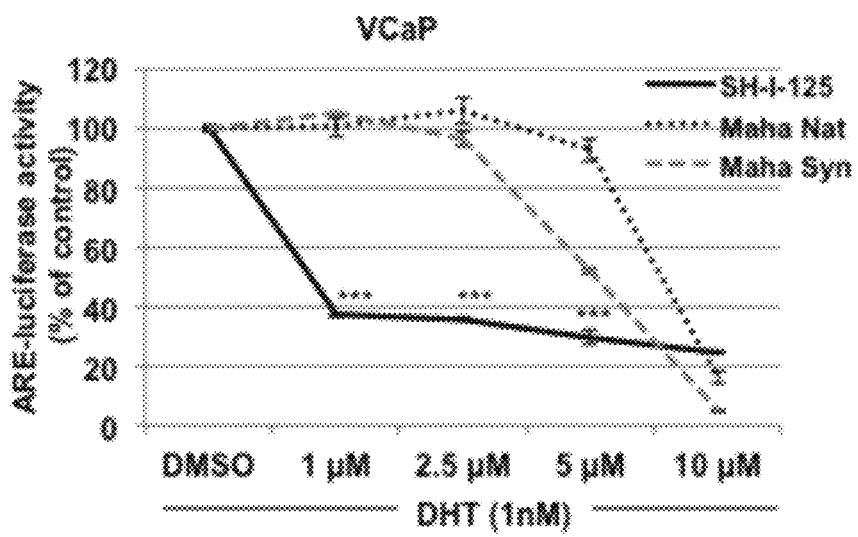
FIG. 3C shows luciferase activity of compounds in VCaP-ARE-luc cells. VCaP-ARE-luc cells were treated with DHT (1 nM) in the absence and presence of a range of doses of SH-I-125, natural mahanine (Maha Nat), and synthetic mahanine (Maha Syn) for 24 hours. Luciferase activity was determined and plotted as a percent of control. Data represent mean of three independent experiments with quadruplicate samples; bars, SEM. ***, p value <0.001 determined by ANOVA.
Figure 3D:
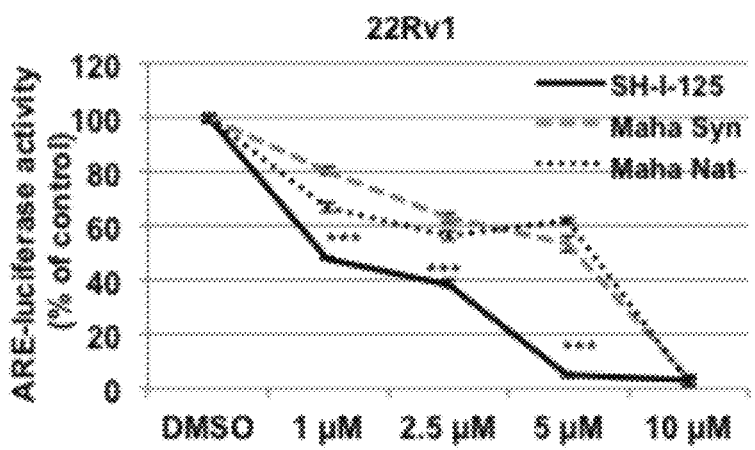
FIG. 3D shows luciferase activity of compounds in 22Rv1-ARE-luc cells. 22Rv1-ARE-luc cells were treated with a range of doses of SH-I-125, natural mahanine (Maha Nat), and synthetic mahanine (Maha Syn) for 24 hours and luciferase activity was determined and plotted as a percent of control. Data represent the mean of three independent experiments with quadruplicate samples; bars, SEM. ***, p value <0.001 determined by ANOVA.

Since both SH-I-125 and mahanine are carbazoles (FIG. 3A), their relative abilities to inhibit growth and AR signaling were assessed. SH-I-125 was found to be ten-fold more potent than natural-derived and synthetically-derived mahanine in preventing the growth of androgen-independent 22Rv1 prostate cancer cells (FIG. 3B). Androgen-dependent VCaP cells and androgen-independent 22Rv1 cells stably expressing androgen-response element luciferase (ARE-luc) reporter construct were used to compare the effects of SH-I-125 and mahanine on AR signaling. In both cell lines, SH-I-125 was found to be more potent than mahanine (FIGS. 3C and 3D). These data indicate that SH-I-125 is a more potent analogue that is suitable for use in prostate cancer therapy.

Figure 4A:
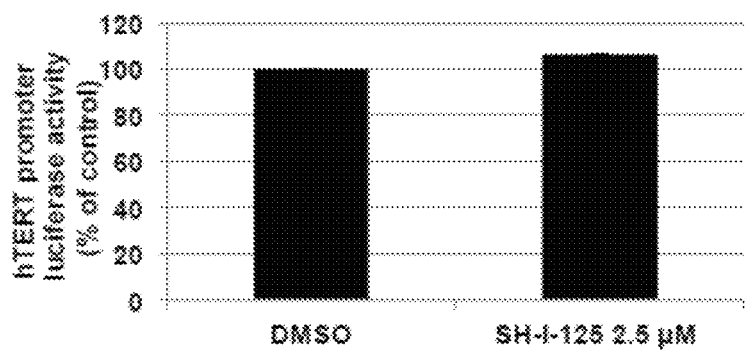
FIG. 4A shows the effect of SH-I-125 on hTERT promoter-luciferase activity. 22Rv1 cells were transfected with hTERT promoter-luciferase reporter construct and Renilla luciferase plasmids (pRL-TK-Luc) and treated with 2.5 µM of SH-I-125 for 24 hours. Promoter activity was determined after normalization with Renilla luciferase activity. Columns, mean of three independent experiments with quadruplicate samples; bars, SEM.
Figure 4B:
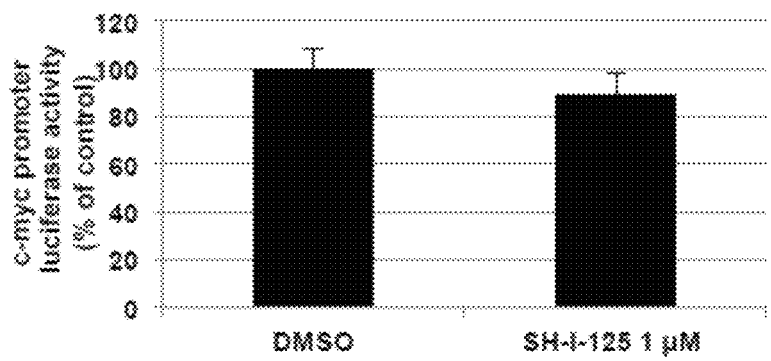
FIG. 4B shows the effect of SH-I-125 on c-myc promoter-luciferase activity. 22Rv1 cells were transfected with c-myc promoter-luciferase reporter construct and Renilla luciferase plasmids (pRL-TK-Luc) and treated with 1 µM of SH-I-125 for 24 hours. Promoter activity was determined after normalization with Renilla luciferase activity. Columns, mean of three independent experiments with quadruplicate samples; bars, SEM.
Figure 4C:
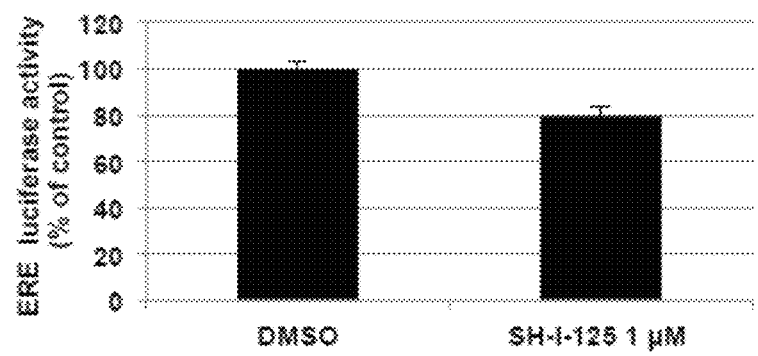
FIG. 4C shows the effect of SH-I-125 on ERE promoter-luciferase activity. 22Rv1 cells were transfected with ERE promoter-luciferase reporter construct and Renilla luciferase plasmids (pRL-TK-Luc) and treated with 1 µM of SH-I-125 for 24 hours. Promoter activity was determined after normalization with Renilla luciferase activity. Columns, mean of three independent experiments with quadruplicate samples; bars, SEM.

To confirm that SH-I-125 does not ubiquitously and non-specifically inhibit the promoter-luciferase activity of other genes, 22Rv1 cells expressing hTERT promoter-luciferase reporter, c-myc promoter luciferase, or estrogen response element-luciferase were treated with SH-I-125. As shown in FIGS. 4A, 4B, and 4C, the luciferase activities of these genes were unaffected.

SH-I-125 has Inhibitory Activity on AR Signaling in Androgen-Dependent Cells Comparable to Second Generation Anti-Androgens, MDV3100 and ARN-509.

Figure 5A:
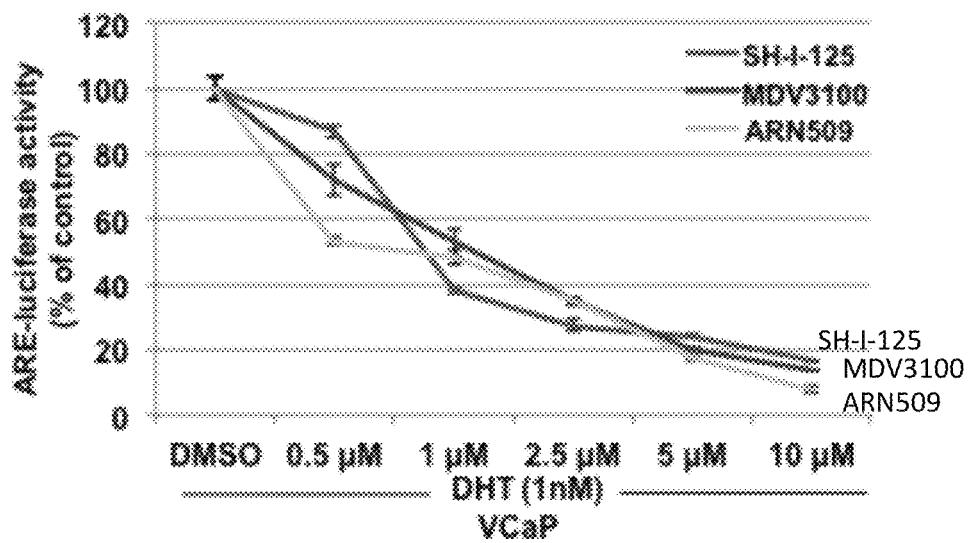
FIG. 5A shows luciferase activity of compounds in VCaP-ARE-luc cells. VCaP-ARE-luc cells were treated with indicated doses of SH-I-125, MDV3100, and ARN-509 in the presence of DHT (1 nM) for 24 hours. Luciferase activity was measured as a percent of control. Data represent mean of three independent experiments with quadruplicate samples; bars, SEM.
Figure 5B:
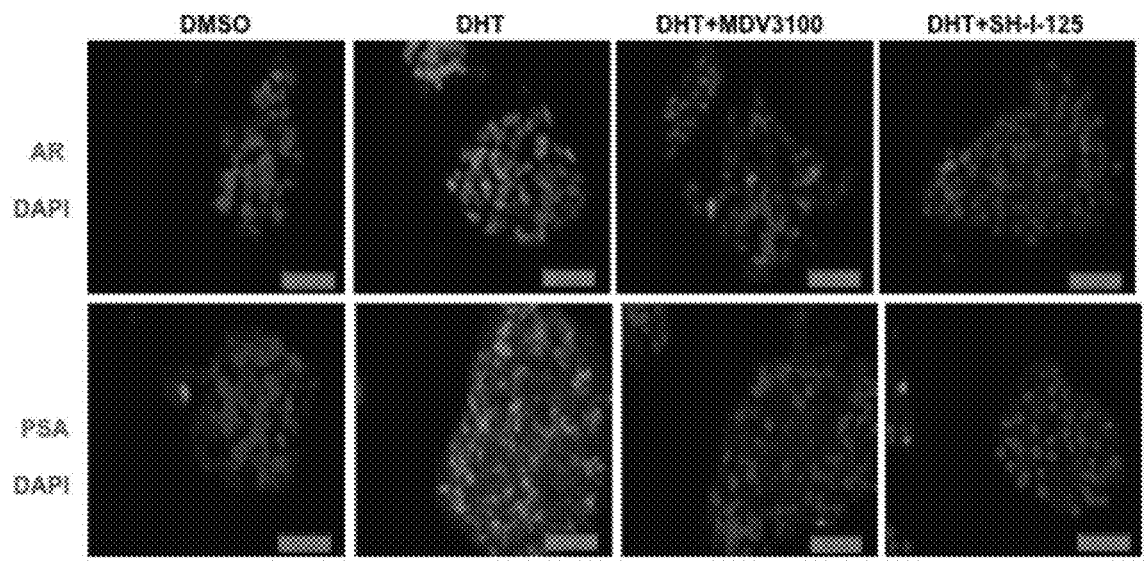
FIG. 5B shows immunofluorescence staining of VCaP cells treated with DHT (1 nM) in the absence and presence of MDV3100 (10 µM) or SH-I-125 (1 µM) for 24 hours. Androgen receptor (AR) and PSA expression levels were assessed.
Figure 5C:
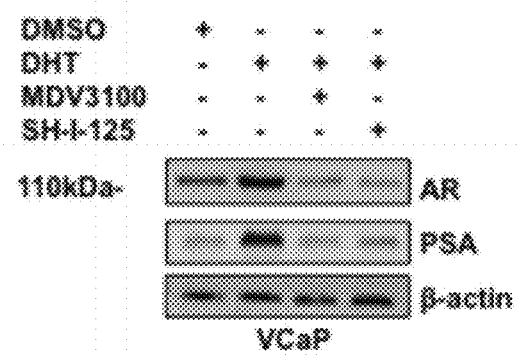
FIG. 5C shows Western blots of VCaP cells treated with MDV3100 (10 µM) or SH-I-125 (1 µM) for 24 hours in the presence of DHT (1 nM). AR and PSA expression levels were assessed. B-actin was used as a loading control.

MDV3100 and ARN-509 have been shown to be potent anti-androgens by competitive inhibition of AR activation by its ligand, DHT. To establish whether SH-I-125 could similarly disrupt AR signaling, VCaP cells stably expressing ARE-luc reporter (VCaP-ARE-luc) were treated with DHT (1 nM) in the presence of various concentrations of MDV3100, ARN-509, and SH-I-125. MDV3100 and ARN-509 effectively inhibited AR transactivation, evidenced by a linear decline in luciferase activity in the presence of increasing amounts of both MDV3100 and ARN-509. Treatment with a range of doses of SH-I-125 produced a comparable decline in luciferase activity, showing that SH-I-125 possesses the ability to prevent AR activation in a manner similar to MDV3100 and ARN-509 (FIG. 5A). Both MDV3100 and SH-I-125 blocked AR nuclear localization, and therefore inhibited PSA expression in VCaP cells (FIG. 5B and FIG. 5C), confirming the ability of both agents to inhibit ligand-induced AR transactivation in androgen-dependent cells.

SH-I-125 is More Effective than Clinical AR Inhibitors, MDV3100 and ARN-509, in Androgen-Independent Cells.

Figure 6A:
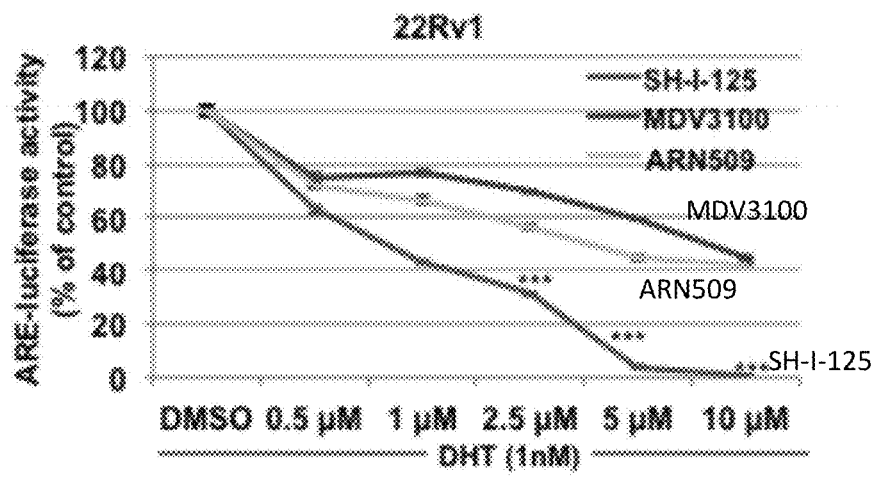
FIG. 6A shows the activity of compounds in 22Rv1-ARE-luc cells. 22Rv1-ARE-luc cells were treated with indicated doses of SH-I-125, MDV3100, and ARN-509 in the presence of DHT (1 nM) for 24 hours. Luciferase activity was measured as a percentage of control. Data represent the mean of three independent experiments with quadruplicate samples; bars, SEM. ***, p value <0.001 determined by ANOVA.
Figure 6B:
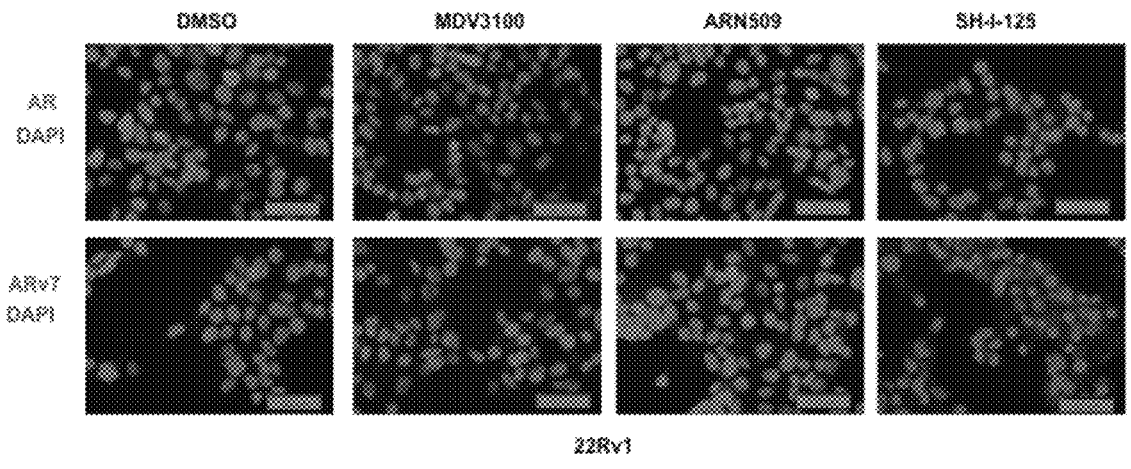
FIG. 6B shows immunofluorescence staining of 22Rv1 cells treated with MDV3100 (10 µM), ARN-509 (10 µM), or SH-I-125 (1 µM) for 24 hours. Androgen receptor (AR) and PSA expression levels were assessed.

22Rv1 cells represent a commonly observed castration-resistant phenotype, including androgen-independent growth and the expression of AR splice variants, such as AR-V7. To determine whether MDV3100 and ARN-509 could disrupt AR activation in this cell type, 22Rv1 cells stably expressing ARE-luc reporter (22Rv1-ARE-luc) cells were treated with MDV3100 and ARN-509. The inhibitory effects of these anti-androgens plateaued at 50% and did not decrease to baseline, as seen in androgen-dependent VCaP-ARE-luc cells (FIG. 6A). However, treatment with SH-I-125 was as effective as seen with VCaP-ARE-luc cells, almost completely abolishing ARE-luciferase activity, showing that SH-I-125 is equally effective in androgen-dependent and androgen-independent prostate cancer cells, and overall SH-I-125 is a more effective AR inhibitor than MDV3100 and ARN-509 (FIG. 6A). Unlike MDV3100 or ARN-509, SH-I-125 decreased the nuclear localization of AR and AR-V7 in 22Rv1 cells, further confirming the ability of SH-I-125 to inhibit AR activity in an androgen-independent cell type (FIG. 6B).

Figure 6C:
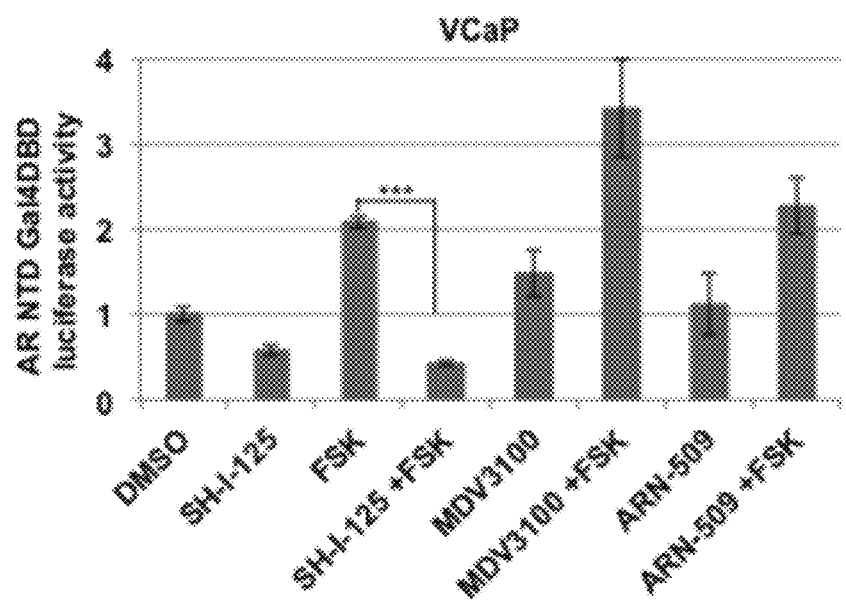
FIG. 6C shows luciferase activity of compounds SH-I-125, MDV3100, and ARN-509 in VCaP cells. VCaP cells were co-transfected with AR-NTD-Gal4DBD expression vector and Gal4UAS-TATA-luciferase reporter construct and optionally treated with forskolin (FSK) (50 µM) for 24 hours. Luciferase activity was measured after normalization with Renilla luciferase. ***, p value <0.001 determined by ANOVA.
Figure 7:
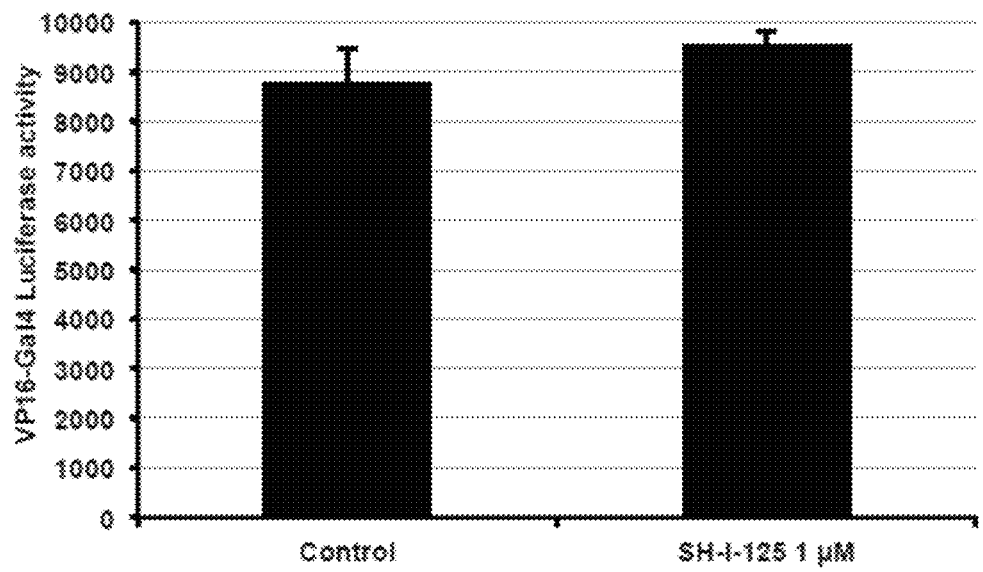
FIG. 7 shows the effect of SH-I-125 on VP16-Gal4DBD activity. 22Rv1 cells were co-transfected with VP16 activation domain-Gal4DBD fusion protein and Gal4UAS-TATA-luciferase reporter and treated with SH-I-125 (1 µM) for 24 hours. Luciferase activity was measured and normalized with Renilla luciferase. Columns, mean of three independent experiments with quadruplicate samples; bars, SEM.

The N-terminal domain of the AR (AR NTD) is known to be its transactivation domain, essential for ligand-independent AR activation. Mahanine is able to inhibit AR activation induced by ligand-independent mechanisms such as forskolin and interleukin-6, which activate the AR NTD. In VCaP cells, which were made to co-express an AR NTD-Gal4-DNA binding domain (AR NTD-Gal4DBD) fusion protein and a luciferase reporter containing the Gal4 binding site (UAS-Luc), SH-I-125 significantly inhibited forskolin-induced AR activation (FIG. 6C). As a negative control, a constitutively active VP16-Gal4DBD fusion protein and the UAS-luc reporter were co-expressed in VCaP cells. It was found that SH-I-125 did not affect luciferase activity, showing that its effects on the AR NTD are independent of any effect on the Gal4DBD (FIG. 7). MDV3100 and ARN-509, which specifically target the AR ligand binding domain (AR LBD), were found to increase forskolin-induced AR activation by an unknown mechanism (FIG. 6C). These results indicate that SH-I-125 is effective in disrupting ligand-independent activation of the AR, and that clinical anti-androgens, MDV3100 and ARN-509, are not effective in disrupting ligand-independent activation of the AR.

SH-I-125 Inhibits Growth in Castration-Resistant Prostate Cancer (CRPC) Cells, but not in Non-Tumorigenic Primary Prostate Epithelial Cells.

Figure 8A:
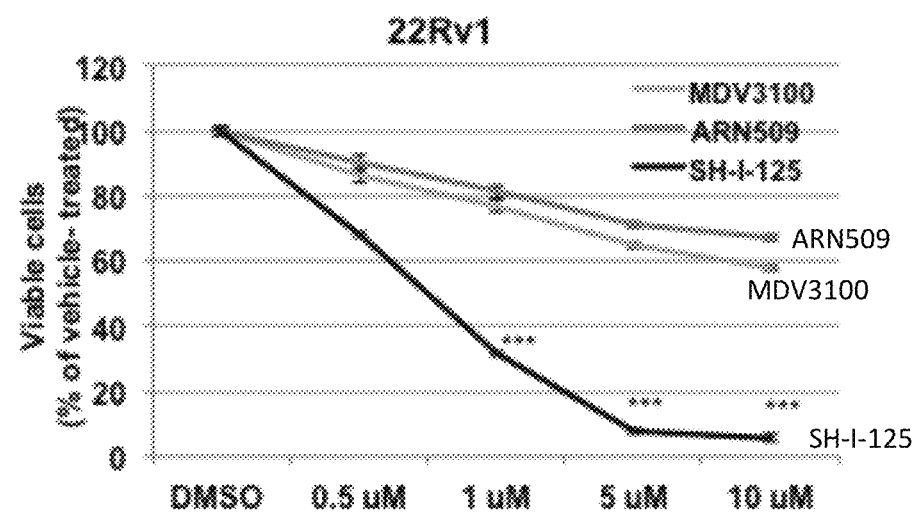
FIG. 8A shows cell viability as determined by MTT assay. 22Rv1 cells were treated with the indicated doses of SH-I-125, MDV3100, or ARN-509 for 3 days. Data represent mean of three independent experiments with quadruplicate samples; bars, SEM. ***, p value <0.001 determined by ANOVA.
Figure 8B:
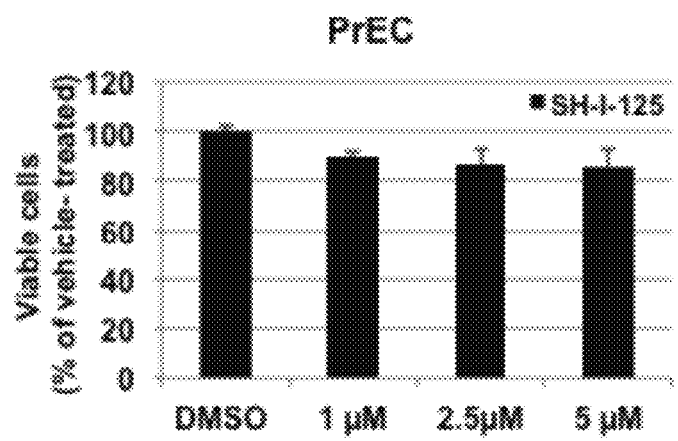
FIG. 8B shows cell viability as determined by MTT assay for PrEC cells treated with the indicated doses of SH-I-125 for 3 days. Data represent mean of three independent experiments with quadruplicate samples; bars, SEM. ***, p value <0.001 determined by ANOVA.
Figure 9A:
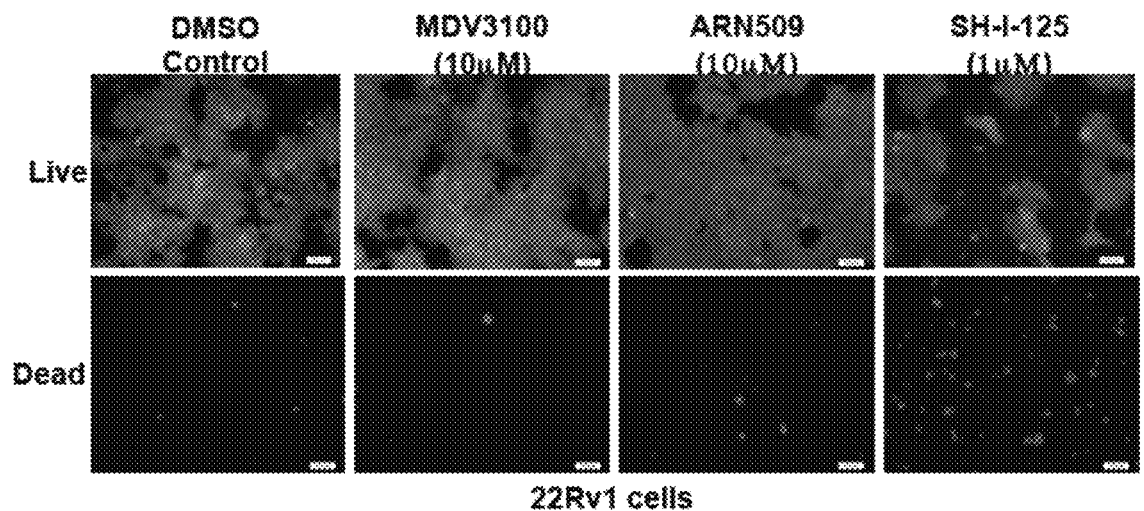
FIG. 9A shows live and dead cell staining of 22Rv1 cells treated with SH-I-125 (1 µM), MDV3100 (10 µM), and ARN-509 (10 µM) for 3 days.
Figure 9B:
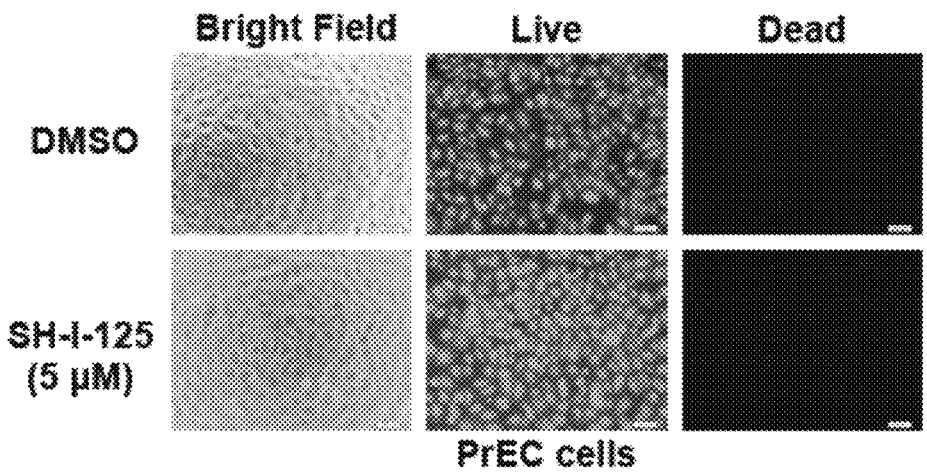
FIG. 9B shows live and dead cell staining of PrEC cells treated with SH-I-125 (5 µM) for 3 days.
Figure 9C:
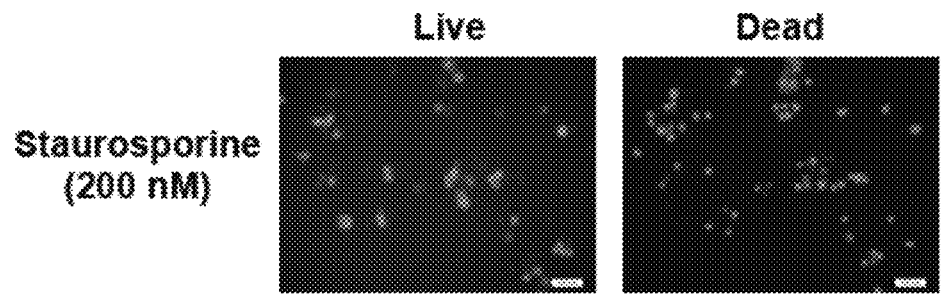
FIG. 9C shows live and dead cell staining results of 22Rv1 cells treated with staurosporine for 4 hours.

To determine the effects of SH-I-125 on prostate cancer cell growth, 22Rv1 cells were treated with SH-I-125 and cell viability was measured after a period of 3 days. It was found that at a dose of 1 µM, cell viability was reduced to 50% of control in the presence of SH-I-125, while MDV3100 and ARN-509 were significantly less effective in preventing the growth of 22Rv1 cells (FIG. 8A). In comparison, non-tumorigenic primary prostate epithelial cells (PrEC) retained 80% viability in the presence of a similar range of doses of SH-I-125, showing that tumorigenic cells are more susceptible to the growth inhibitory properties of SH-I-125 compared to non-tumorigenic cells (FIG. 8B). In addition, upon staining to specifically detect live and dead cells upon SH-I-125 treatment, it was found that although SH-I-125 killed 22Rv1 cells, PrEC were mostly unaffected, in spite of the five-fold higher dose used to treat PrEC compared to 22Rv1 (FIGS. 9A and 9B). Staurosporine was used as a positive control for cell death induction in live and dead assays (FIG. 9C). Together, these data confirmed that SH-I-125 has differential cytotoxic effects on tumorigenic versus non-tumorigenic cells.

SH-I-125, but not MDV3100 and ARN-509, Induces Caspase-Mediated Apoptosis in Prostate Cancer Cells.

Figure 8C:
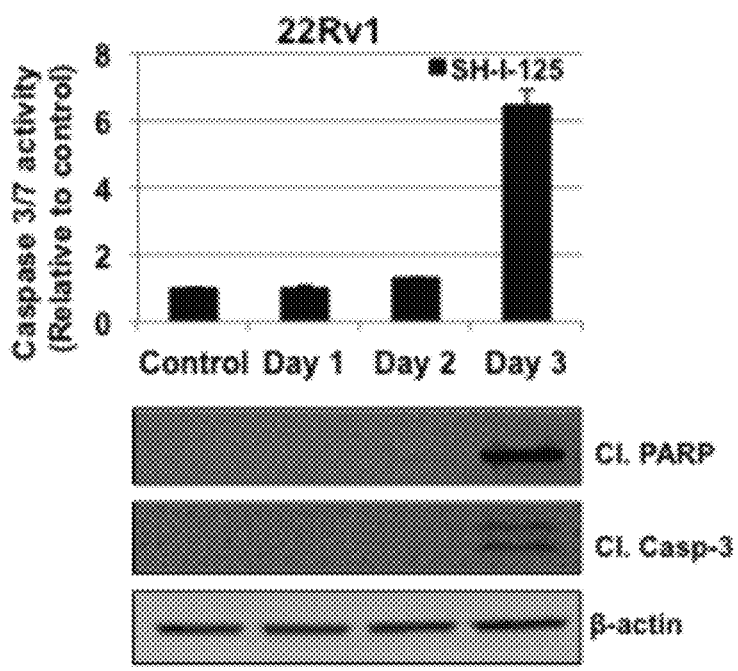
FIG. 8C, upper panel, shows caspase 3/7 activity for compounds in 22Rv1 cells. 22Rv1 cells were treated with SH-I-125 (1 µM) for one, two, or three days, and caspase 3/7 activity was measured using Caspase-Glo 3/7 substrates.
Figure 10A:
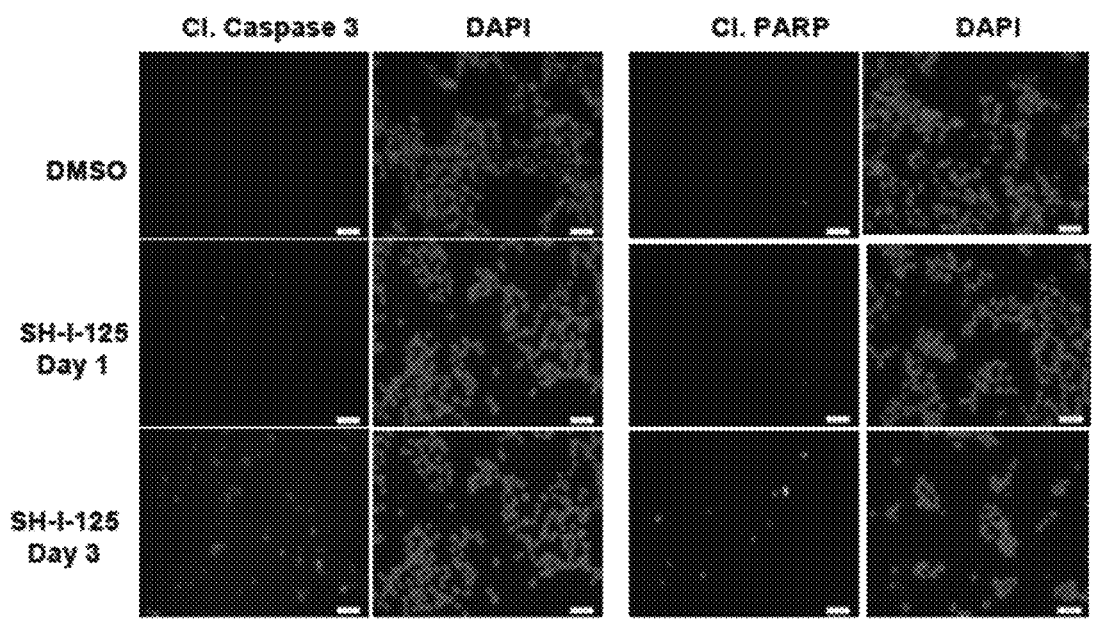
FIG. 10A shows immunofluorescence staining of 22Rv1 cells treated with SH-I-125 (1 µM) for three days. The presence of cleaved caspase-3 and cleaved PARP were determined. The cells were counterstained with 4',6-diamidino-2-phenylindole (DAPI).
Figure 10B:
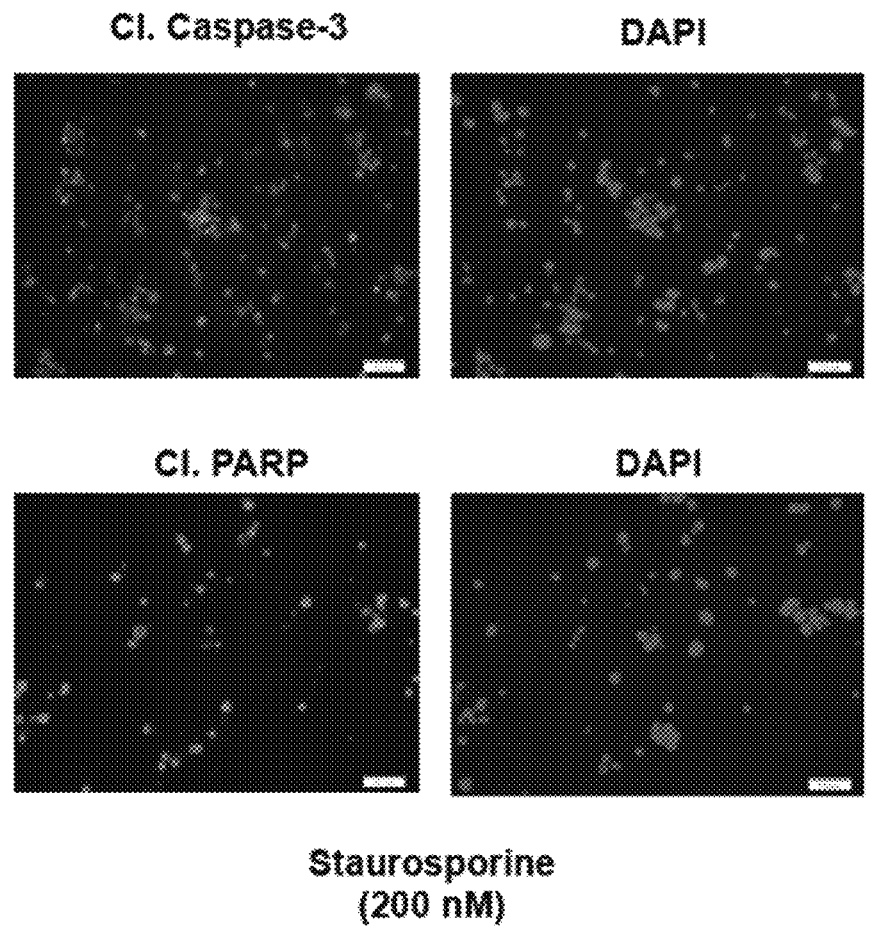
FIG. 10B shows immunofluorescence staining of 22Rv1 cells treated with staurosporine (200 nM) for four hours. The presence of cleaved caspase-3 and cleaved PARP was determined. The cells were counterstained with 4',6-diamidino-2-phenylindole (DAPI).

It was determined whether caspase activity and apoptosis were induced in 22Rv1 cells upon SH-I-125 treatment. A time-course of SH-I-125 treatment revealed that caspase-3 and -7 activities were significantly induced in 22Rv1 cells after three days treatment. Caspase activation was confirmed by the presence of cleaved caspase-3 and accompanied by the cleavage of PARP, a well-known target of caspase-3, after three days of SH-I-125 treatment (FIG. 8C and FIG. 10A). Staurosporine was used as a positive control for apoptosis induction (FIG. 10B).

Figure 8D:
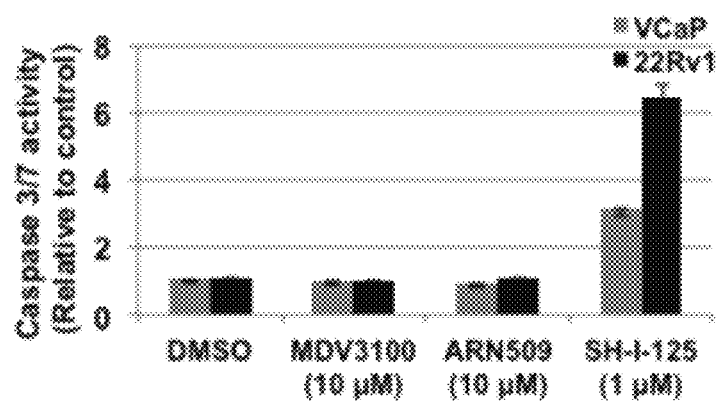
FIG. 8D shows caspase 3/7 activity for compounds in VCaP and 22Rv1 cells. VCaP cells and 22Rv1 cells were treated with MDV3100, ARN-509 and SH-I-125 for 3 days. Caspase 3/7 activity was measured using Caspase-Glo 3/7 substrates. Data represent mean of three independent experiments with quadruplicate samples; bars, SEM. ***, p value <0.001 determined by ANOVA.

While SH-I-125 induced caspase activity in both androgen-dependent VCaP cells and androgen-independent 22Rv1 cells, MDV3100 and ARN-509 did not have a similar effect in either cell line, showing that these anti-androgens are ineffective in inducing caspase-mediated cell death in androgen-dependent and androgen-independent prostate cancer cells (FIG. 8D).

SH-I-125, but not MDV3100 and ARN-509, Reduces Cellular Levels of AR and AR-V7 by Proteasomal Degradation.

Figure 11:
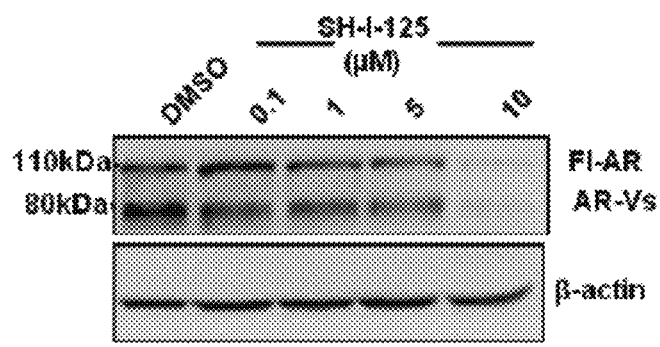
FIG. 11 shows the effect of SH-1-125 on AR levels in 22Rv1 cells. 22Rv1 cells were treated with the indicated doses of SH-I-125 for 3 days. AR levels were assessed by Western blotting. β-actin was used as a loading control.
Figure 12A:
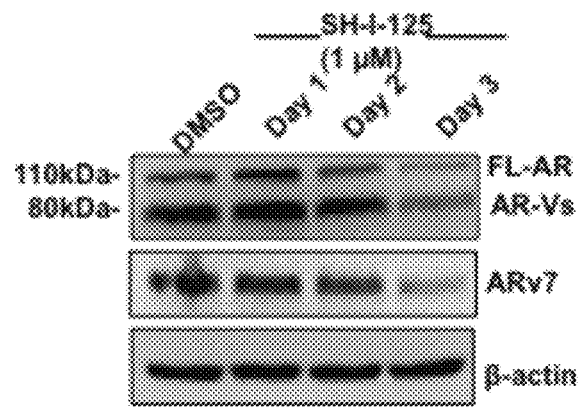
FIG. 12A shows Western blots of 22Rv1 cells treated with 1 µM SH-I-125 for 1-3 days. AR and AR-V7 levels were assessed. β-actin was used as a loading control.
Figure 12B:
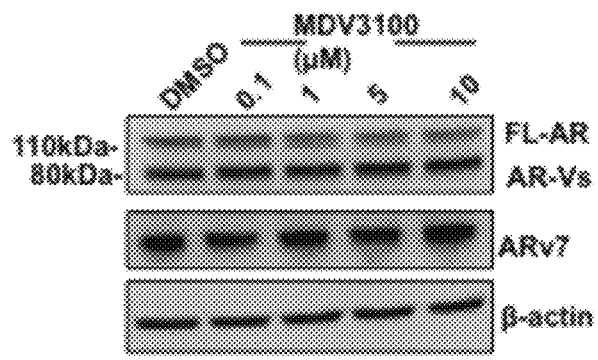
FIG. 12B shows Western blots of 22Rv1 cells treated with the indicated amounts of MDV3100 for 1-3 days. AR and AR-V7 levels were assessed. β-actin was used as a loading control.
Figure 12C:
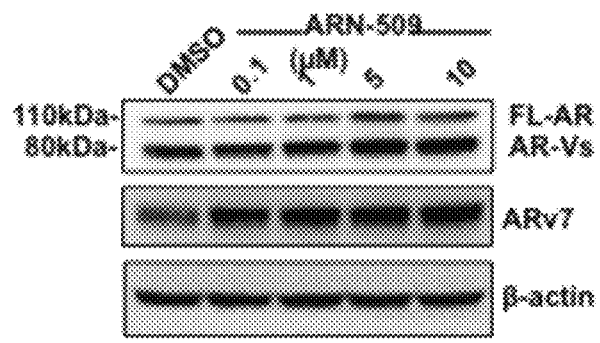
FIG. 12C shows Western blots of 22Rv1 cells treated with the indicated amounts of ARN-509 for 1-3 days. AR and AR-V7 levels were assessed. β-actin was used as a loading control.

To determine whether SH-I-125 affected the cellular levels of the AR and its splice variants, 22Rv1 cells were treated with a range of doses of SH-I-125 for 3 days, and 1 µM SH-I-125 for 1-3 days (FIG. 11 and FIG. 12A). Additionally, 22Rv1 cells were treated with a range of doses of MDV3100 and ARN-509 for a period of 3 days (FIGS. 12B and 12C). While MDV3100 and ARN-509 had no effect on AR and AR-V7 levels, SH-I-125 reduced AR and AR-V7 levels at a dose of 1 µM in a period of 3 days, indicating that in addition to inhibition of AR activity, SH-I-125 was effective in declining the cellular levels of the AR and its splice variant.

Figure 12D:
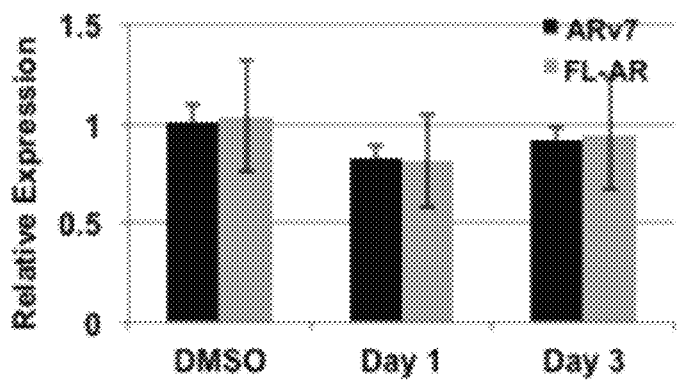
FIG. 12D is a graph showing the mRNA expression of AR and AR-V7 after treating 22Rv1 cells with SH-I-125 (1 µM) for 24 and 72 hrs. The AR and AR-V7 expression levels were assessed by qRTPCR and normalized to GAPDH expression levels.
Figure 12E:
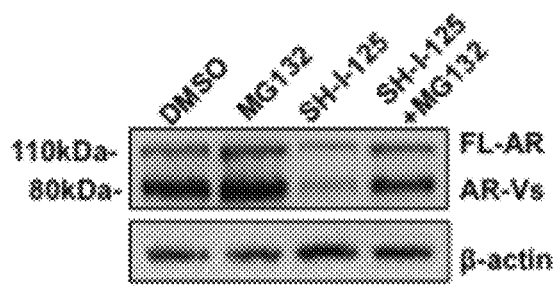
FIG. 12E shows Western blots of 22Rv1 cells treated with SH-I-125 (1 µM) for a period of 3 days. MG132 (5 µM), a known proteasome inhibitor, was added on Day 2. AR expression was assessed by Western blotting. β-actin was used as a loading control.

To establish a mechanism by which SH-I-125 caused a decline in AR and AR-V7 levels, the relative expression of AR and AR-V7 in 22Rv1 cells that had been treated with SH-I-125 for a period of 1-3 days was measured. The data show that SH-I-125 did not affect the message levels of these genes, demonstrating that AR and AR-V7 decline post-translationally in cells treated with SH-I-125 (FIG. 12D). To determine whether proteasomal mechanisms are responsible for the decline in AR and AR-V7 levels, 22Rv1 cells were treated with 5 µM SH-I-125 for a period of 48 hours in the presence of proteasome inhibitor, MG132. Proteasome inhibition rescued the decline in AR and AR splice variant levels in the presence of SH-I-125 (FIG. 12E), showing that SH-I-125 induces proteasomal degradation of AR and its splice variant.

SH-I-125 Prevents the Growth of Prostate Cancer Cells that are Resistant to Clinical Anti-Androgens.

Figure 13A:
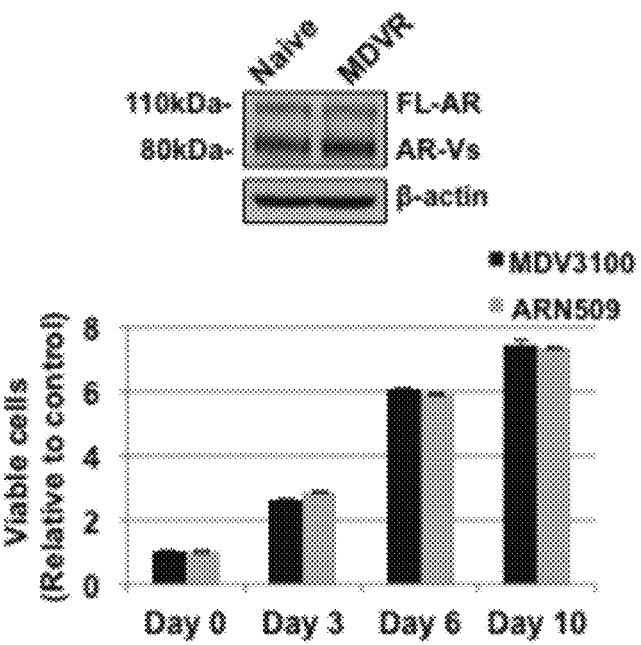
FIG. 13A, upper panel, shows Western blots depicting AR expression as evaluated in 22Rv1-MDVR cells.
Figure 13B:
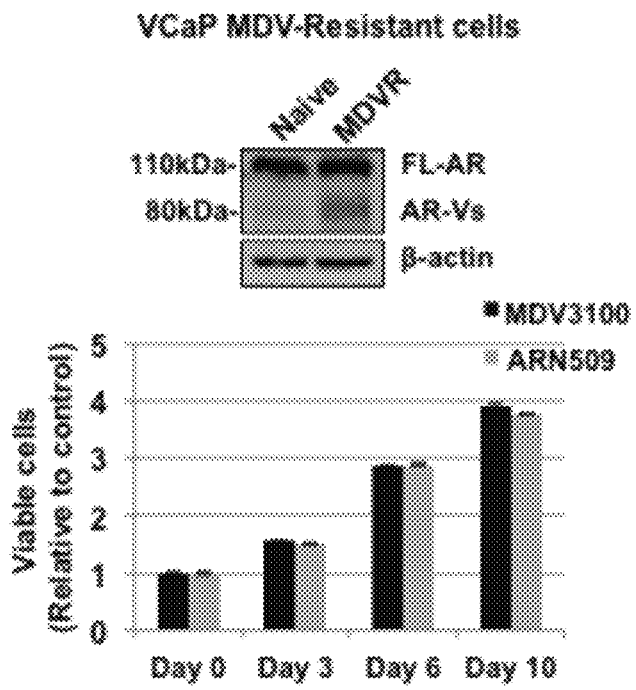
FIG. 13B, upper panel, shows Western blots depicting AR expression as evaluated in VCaP-MDVR cells.
Figure 13C:
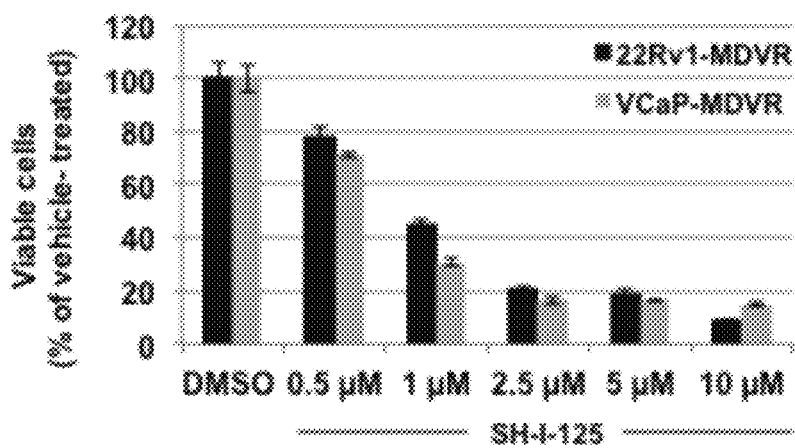
FIG. 13C is a graph showing cell viability after treating 22Rv1-MDVR and VCaP-MDVR cells with the indicated concentrations of SH-I-125 for 3 days. Cell viability was measured using the MTT assay. Data represent mean of three independent experiments with quadruplicate samples; bars, SEM.
Figure 13D:
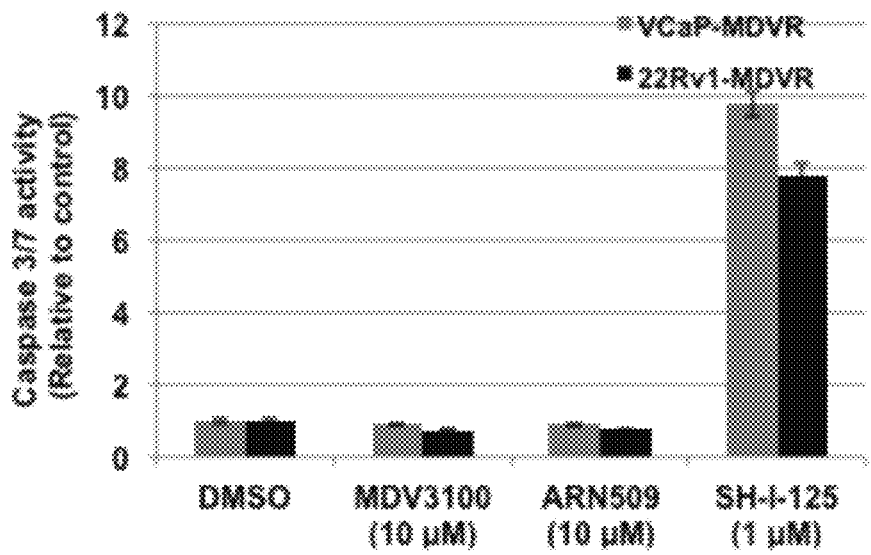
FIG. 13D is a graph showing caspase 3/7 activity after treating VCaP-MDVR and 22Rv1-MDVR cells with MDV3100 (10 µM), ARN509 (10 µM) and SH-I-125 (1 µM) for 3 days. Caspase 3/7 activity was measured using Caspase-Glo 3/7 substrates. Data represent mean of three independent experiments with quadruplicate samples; bars, SEM.

The emergence of resistance to clinical anti-androgens is an ongoing problem in the treatment of castration-resistant prostate cancer. To establish whether SH-I-125 can prevent the growth of drug-resistant prostate cancer cells, VCaP- and 22Rv1-MDV3100-resistant cells (VCaP-MDVR and 22Rv1-MDVR) were generated by prolonged culturing of these cell lines in the presence of MDV3100 (details described above in the Materials and Methods section). VCaP-MDVR cells showed increased expression of AR splice variants compared to naïve control, whereas no change was observed in splice variants in 22Rv1-MDVR cells (FIG. 13A, upper panel and FIG. 13B, upper panel). Both VCaP and 22Rv1 cells acquired resistance to clinical anti-androgens, evidenced by their continued proliferation in the presence of MDV3100 and ARN-509 (FIG. 13A, lower panel and FIG. 13B, lower panel). However, treatment of VCaP-MDVR and 22Rv1-MDVR cells with SH-I-125 showed that the compound was effective in preventing the growth and inducing caspase activation in both the drug-resistant cell lines (FIG. 13C and FIG. 13D).

Drug-Resistant Cells Retain AR Activity in the Presence of Clinical Anti-Androgens, but not Upon Treatment with SH-I-125.

Figure 14A:
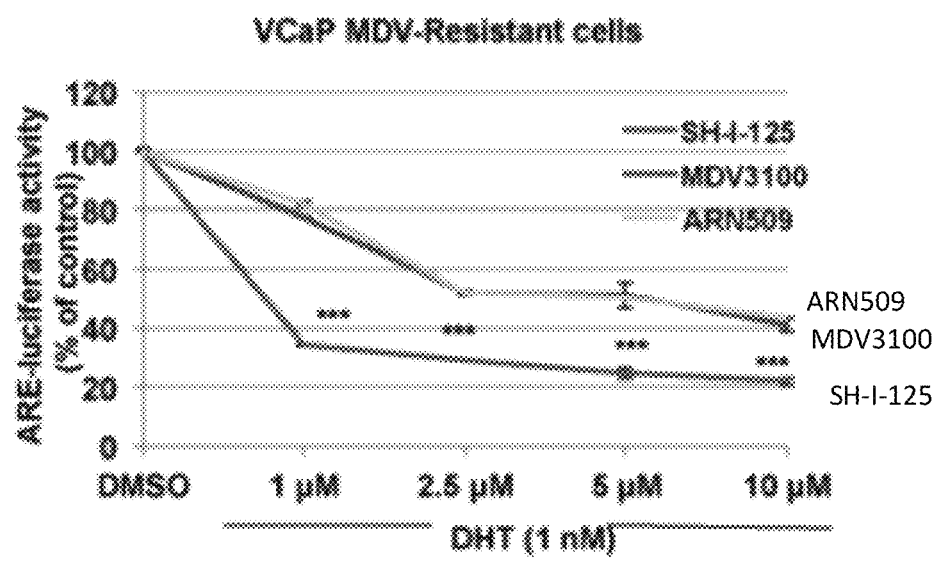
FIG. 14A is a graph showing the luciferase activity of VCaP-MDVR-ARE-luc cells treated with a range of doses of MDV3100, ARN509, and SH-I-125 for 24 hours. Luciferase activity was measured and plotted as a percentage of control. Data represent the mean of three independent experiments with quadruplicate samples; bars, SEM. ***, p value <0.001 determined by ANOVA.
Figure 14B:
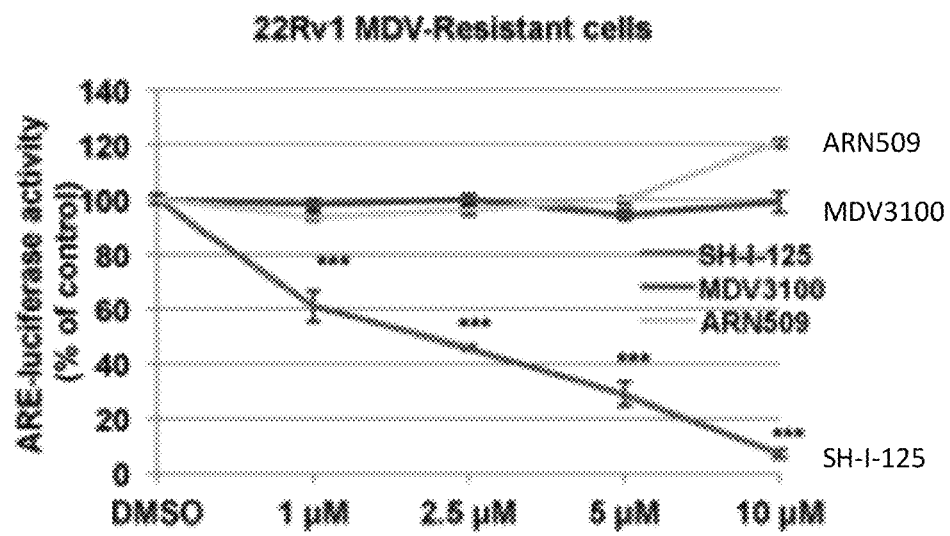
FIG. 14B is a graph showing the activity of 22Rv1-MDVR-ARE-luc cells treated with a range of doses of MDV3100, ARN509 and SH-I-125 for 24 hours. Luciferase activity was measured and plotted as a percentage of control. Data represent the mean of three independent experiments with quadruplicate samples; bars, SEM. ***, p value <0.001 determined by ANOVA.

VCaP-MDVR and 22Rv1-MDVR stably expressing ARE-luciferase construct (VCaP-MDVR-ARE-luc and 22Rv1-MDVR-ARE-luc) were generated as described above in the Materials and Methods section. Luciferase activity, a measure of AR activation, was only reduced by 50% in VCaP-MDVR-ARE-luc cells by MDV3100 and ARN-509 treatment, which is in contrast to an approximate 80% reduction in VCaP-ARE-luc cells (FIG. 14A and FIG. 5A). Similarly, in 22Rv1-MDVR-ARE-luc cells, luciferase activity remained unchanged from control upon treatment with a range of doses of MDV3100 and ARN-509, which is in contrast to the decrease in luciferase activity seen in 22Rv1-ARE-luc cells treated in the same manner (FIG. 14B and FIG. 6A). However, SH-I-125 retained its inhibitory effect on AR activity in both drug-resistant cell lines.

Figure 14C:
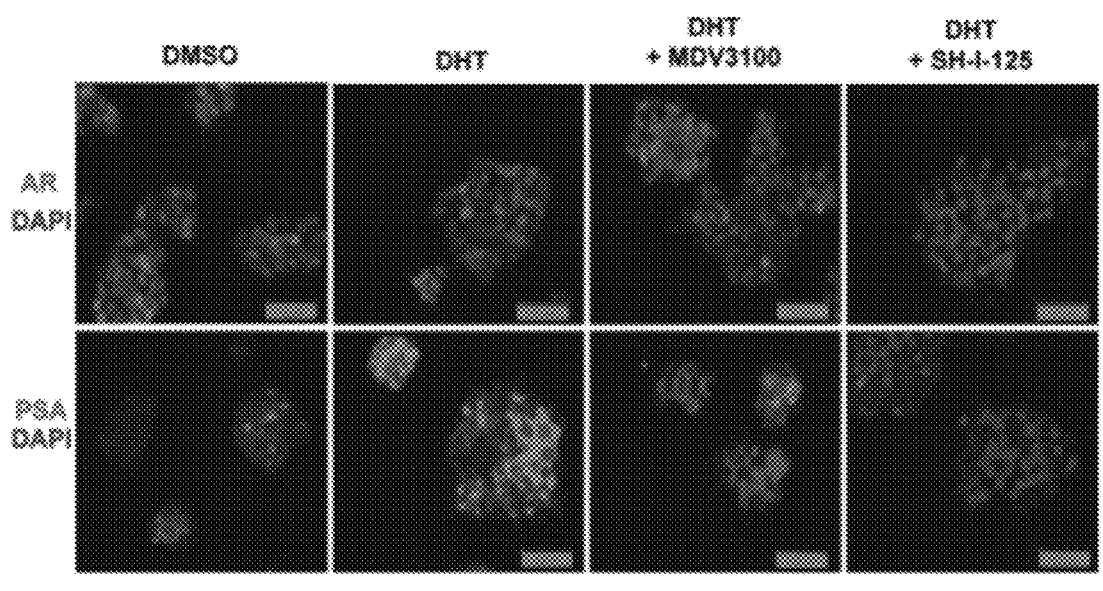
FIG. 14C shows immunofluorescence staining of VCaP-MDVR cells treated with DHT (1 nM) in the absence and presence of MDV3100 (10 µM) or SH-I-125 (1 µM) for 24 hours. AR and PSA expression levels were assessed.

Furthermore, while MDV3100 continued to inhibit PSA expression in VCaP-MDVR cells, AR expression was not attenuated as seen before in naïve-VCaP cells (FIG. 14C and FIG. 5B), showing that, although AR activity is partially reduced, as evidenced by decreased PSA expression, its continued expression indicates that it could be involved in mediating alternative transcriptional programs. SH-I-125 decreased AR nuclear localization and PSA expression in VCaP-MDVR cells in a manner similar to that seen in naïve-VCaP cells.

Figure 14D:
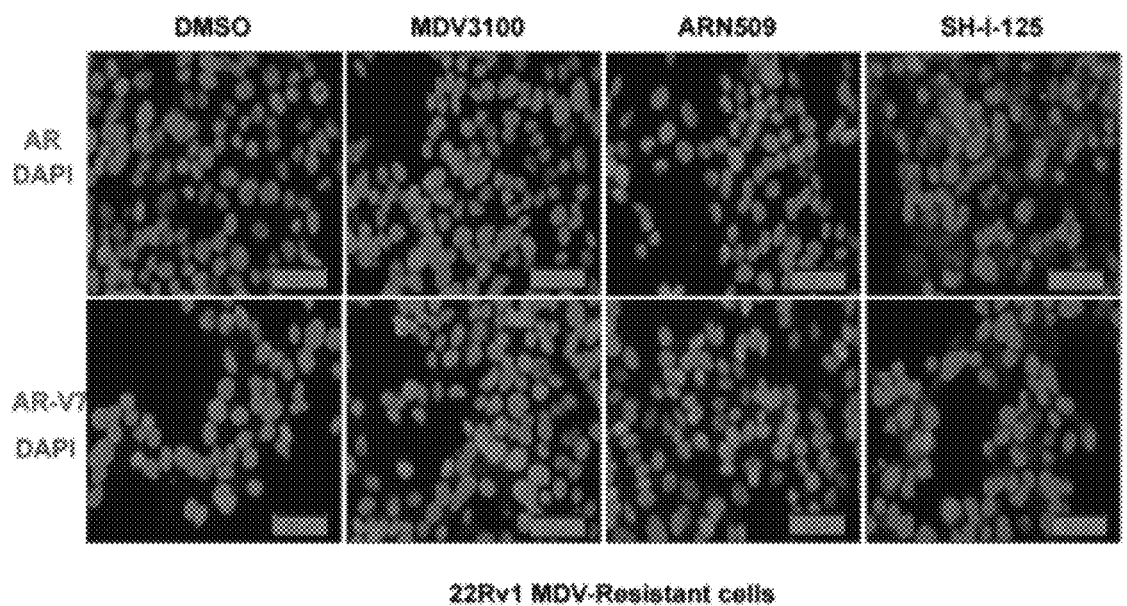
FIG. 14D shows immunofluorescence staining of 22Rv1-MDVR cells treated with MDV3100 (10 µM), ARN509 (10 µM), or SH-I-125 (1 µM) for 24 hours. AR and AR-V7 expression levels were assessed.

Although AR nuclear localization remained unaffected by MDV3100 and ARN-509 treatment, SH-I-125 treatment decreased AR nuclear levels and caused it to translocate to the cytoplasm in 22Rv1-MDVR cells (FIG. 14D), showing that SH-I-125 has the ability to decrease nuclear localization of AR and its splice variants in androgen-independent and anti-androgen-resistant prostate cancer cells.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound selected from the group consisting of:

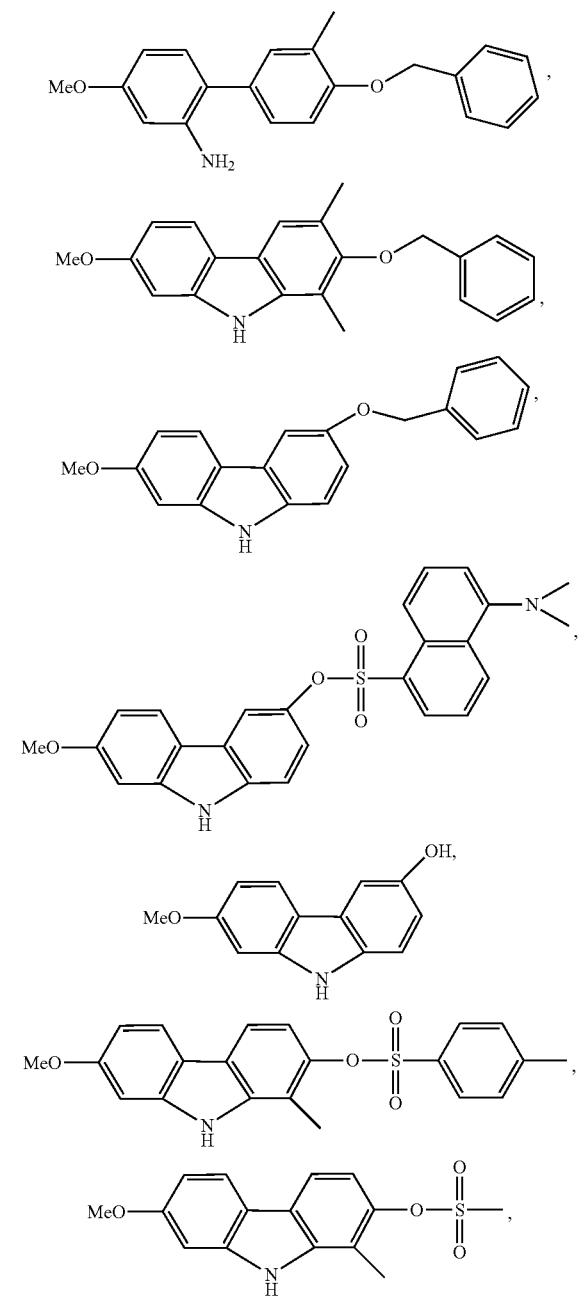

31
-continued

32
-continued

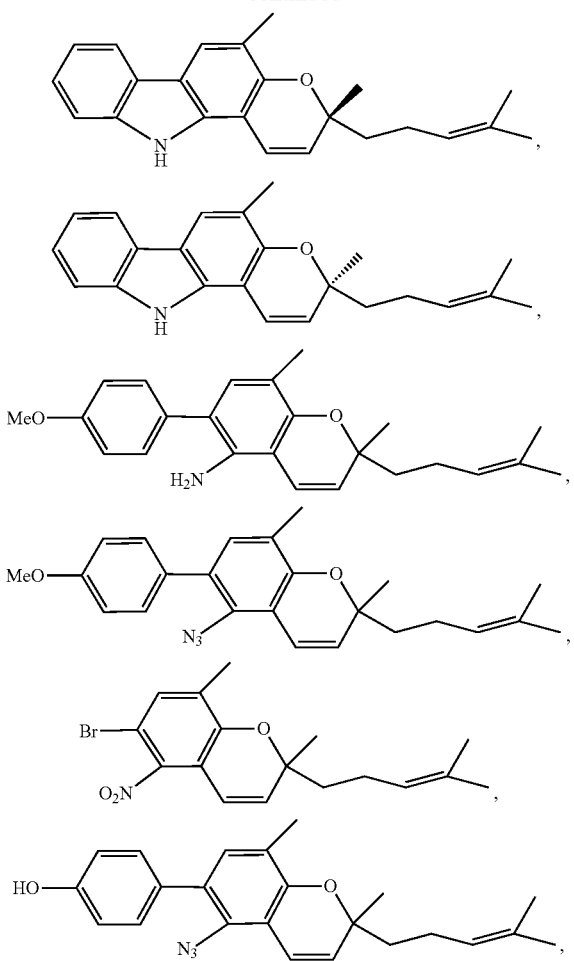

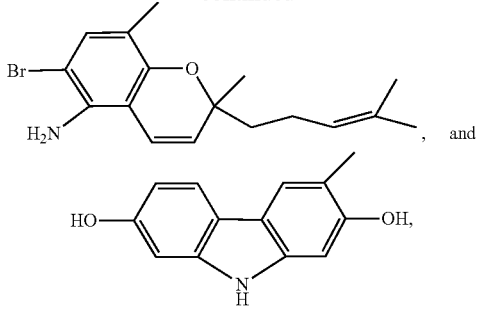

or a pharmaceutically acceptable salt thereof.

2. A composition comprising a compound of claim 1 and a pharmaceutically acceptable carrier.

3. A method of treating prostate cancer in a subject, comprising administering to the subject an effective amount of the composition of claim 2.

4. The method of claim 3, wherein the prostate cancer is a castration-resistant prostate cancer or a drug-resistant cancer.

5. The method of claim 3, wherein the prostate cancer is androgen-independent prostate cancer or androgen-dependent prostate cancer.

6. The method of claim 3, further comprising administering a second therapeutic agent to the subject, wherein the second therapeutic agent is a chemotherapeutic agent.

7. A method of inhibiting androgen receptor activity in a cell, comprising contacting the cell with an effective amount of the compound of claim 1.

8. The method of claim 7, wherein the cell is an androgen-dependent cell or an androgen-independent cell.

9. The method of claim 7, wherein the contacting is performed in vivo.

10. The method of claim 7, wherein the contacting is performed in vitro.

* * * * *